(12) United States Patent
Rupnow et al.

(10) Patent No.: US 11,331,398 B2
(45) Date of Patent: May 17, 2022

(54) SYSTEMS AND METHODS FOR SANITIZING A LAUNDRY SLING

(71) Applicant: OMNI SOLUTIONS LLC, Baraboo, WI (US)

(72) Inventors: Andrew Rupnow, Wisconsin Dells, WI (US); Paul Jewison, Chatfield, MN (US)

(73) Assignee: OMNI SOLUTIONS LLC, Baraboo, WI (US)

(*) Notice: Subject to any disclaimer, the term of this patent is extended or adjusted under 35 U.S.C. 154(b) by 125 days.

(21) Appl. No.: 16/618,104

(22) PCT Filed: Jun. 1, 2018

(86) PCT No.: PCT/US2018/035695
§ 371 (c)(1),
(2) Date: Nov. 27, 2019

(87) PCT Pub. No.: WO2018/223061
PCT Pub. Date: Dec. 6, 2018

(65) Prior Publication Data
US 2020/0108162 A1     Apr. 9, 2020

Related U.S. Application Data

(60) Provisional application No. 62/513,885, filed on Jun. 1, 2017.

(51) Int. Cl.
*A61L 2/10*     (2006.01)
*A61L 2/20*     (2006.01)
(Continued)

(52) U.S. Cl.
CPC ............. *A61L 2/10* (2013.01); *A61L 2/084* (2013.01); *A61L 2/085* (2013.01); *A61L 2/202* (2013.01);
(Continued)

(58) Field of Classification Search
None
See application file for complete search history.

(56) References Cited

U.S. PATENT DOCUMENTS

| | | |
|---|---|---|
| 4,309,388 A | 1/1982 | Tenney |
| 4,374,087 A | 2/1983 | Hallstrom |

(Continued)

FOREIGN PATENT DOCUMENTS

| | | |
|---|---|---|
| CN | 201603137 U | 10/2010 |
| JP | 2002-318071 A | 10/2002 |

(Continued)

OTHER PUBLICATIONS

Navy Environmental Health Center, Ultraviolet Radiation Guide, Apr. 1992 (Year: 1992).*

(Continued)

*Primary Examiner* — Holly Kipouros
(74) *Attorney, Agent, or Firm* — Nixon Peabody LLP

(57) ABSTRACT

A sanitizing system for sanitizing a laundry sling that is moveable along one or more support rails includes a motor, a cable operatively coupled to the motor, a sanitizing lamp coupled to the cable, and a controller configured to cause the motor to operate such that the sanitizing lamp is moved, via the cable, from a first position to a second position and actuate the sanitizing lamp such that the sanitizing lamp emits a sanitizing wavelength of light.

13 Claims, 21 Drawing Sheets

(51) Int. Cl.
D06F 95/00 (2006.01)
A61L 2/08 (2006.01)

(52) U.S. Cl.
CPC ........ *A61L 2202/11* (2013.01); *A61L 2202/14* (2013.01); *A61L 2202/16* (2013.01); *A61L 2202/23* (2013.01); *D06F 95/004* (2013.01)

(56) References Cited

U.S. PATENT DOCUMENTS

| | | | |
|---|---|---|---|
| 2011/0126357 A1 | 6/2011 | Hartman | |
| 2013/0039807 A1* | 2/2013 | LeBlanc | A23L 3/12 |
| | | | 422/28 |
| 2013/0330235 A1* | 12/2013 | Stibich | A61L 2/24 |
| | | | 422/105 |
| 2015/0248945 A1* | 9/2015 | Marchesini | A61N 5/01 |
| | | | 250/454.11 |
| 2015/0359915 A1 | 12/2015 | Farren et al. | |
| 2018/0064833 A1* | 3/2018 | Childress | A61L 2/24 |
| 2019/0321502 A1* | 10/2019 | Kim | A61L 2/088 |

FOREIGN PATENT DOCUMENTS

| | | | | |
|---|---|---|---|---|
| JP | 2016-078895 A | 5/2016 | | |
| WO | WO 92/18170 A1 | 10/1992 | | |
| WO | WO-2011055140 A1 * | 5/2011 | ............... | A61L 2/24 |
| WO | WO 2012/166203 A1 | 12/2012 | | |

OTHER PUBLICATIONS

Extended European Search Report in European Patent Application No. EP 18810175.2, dated Mar. 3, 2021 (10 pages).

International Search Report and Written Opinion for PCT/US18/035695 dated Jun. 1, 2018 (14 pages).

* cited by examiner

SYSTEMS AND METHODS FOR SANITIZING A LAUNDRY SLING

CROSS-REFERENCE TO RELATED APPLICATIONS

This application is a U.S. National Stage of International Application No. PCT/US2018/035695, filed Jun. 1, 2018, which claims the benefit of and priority to U.S. Provisional Patent Application No. 62/513,885, filed Jun. 1, 2017, each of which are hereby incorporated by reference herein in their entireties.

FIELD OF THE PRESENT DISCLOSURE

The present disclosure relates generally to sanitizing systems and methods, and more particularly, to systems and methods for sanitizing a laundry sling.

BACKGROUND

In industrial laundry applications, laundry slings, bags, and/or hoppers suspended from one or more support rails are used to transport laundry (i.e., clothes, linens, fabrics, or the like) between various locations in a laundry facility. More specifically, the laundry is loaded into an interior of the laundry sling and moved along the one or more support rails to a desired location. Often, when transporting soiled laundry, the laundry slings become contaminated by bacteria, viruses, fungi, or the like from the soiled laundry. Some facilities use the same laundry slings to transport both soiled and cleaned laundry, thereby potentially cross-contaminating the clean laundry. And when soiled laundry comes from a medical facility, for example, the potential health risks associated with contamination of the laundry slings are even greater.

In an effort to avoid contamination of cleaned laundry, industrial laundry facilities are often divided into a "soiled side" and a "clean side." On the soiled side, a first set of slings are used to sort soiled laundry and transport pre-sorted and weighted laundry between incoming delivery trucks and tunnel washers for cleaning. On the clean side of the facility, a second set of slings transport the washed and dried laundry from dryers to sorters and folders. Yet despite these efforts to prevent contamination of the second set of laundry slings from soiled laundry, these slings can still become contaminated over continued use. For example, cleaned laundry that is still damp when placed in the laundry slings can lead to the growth of bacteria, viruses, fungi (e.g., mold), or the like on the clean side of the facility.

Thus, it is highly desirable to routinely sanitize the laundry slings, even on the clean side of the facility, to prevent contamination of cleaned laundry from the laundry slings. However, for safety purposes, the laundry slings must be securely fastened to the one or more support rails using complex fastening mechanisms. As a result, it is often difficult, time consuming, and highly impractical to routinely remove the laundry slings from the one or more support rails for sanitizing. For this reason, a majority of industrial laundry facilities do not routinely sanitize the laundry slings that transport cleaned laundry, subjecting the cleaned laundry to a continuous threat of cross-contamination from the laundry slings. In other words, without properly sanitizing the laundry slings on the clean side of the facility, there can be no guarantee that the cleaned laundry is completely sanitized, no matter how effective the washers and dryers are. Thus, new systems and methods are needed to quickly and easily sanitize laundry slings in high volumes without needing to remove the slings from the rail support system. The present disclosure addresses these and other problems.

SUMMARY

According to some implementations of the present disclosure, a sanitizing system includes a motor, a cable operatively coupled to the motor, a sanitizing lamp coupled to the cable, and a controller configured to cause the motor to operate such that the sanitizing lamp is moved, via the cable, from a first position to a second position and actuate the sanitizing lamp such that the sanitizing lamp emits a sanitizing wavelength of light.

According to some implementations of the present disclosure, a sanitizing system for use in sanitizing a laundry sling that is moveable along one or more support rails includes a housing, a winding device positioned within the housing and being coupled to a cable, a motor coupled to the housing and the winding device such that the motor is configured to cause the winding device to wind and unwind the cable, a sanitizing lamp coupled to the cable and being configured to emit a sanitizing wavelength of light therefrom, and a controller configured to cause the motor to cause the winding device to at least partially unwind the cable such that at least a portion of the sanitizing lamp protrudes from the housing and is at least partially positioned within the laundry sling and the sanitizing lamp to emit the sanitizing wavelength of light to aid in sterilizing an interior surface of the laundry sling.

According to some implementations of the present disclosure, a system for sanitizing a laundry sling that is moveable along one or more support rails includes an outer housing having an upper portion and a lower portion, an inner track coupled to the outer housing, a transport mechanism coupled to the inner track such that the transport mechanism is moveable relative to the inner track between a first position and a second position, a sanitizing lamp coupled to the transport mechanism such that movement of the transport mechanism from the first position to the second position causes a corresponding movement of the sanitizing lamp, and an actuator coupled to the inner track and the transport mechanism, the actuator being configured to cause the transport mechanism to move from the first position to the second position such that at least a portion of the sanitizing lamp protrudes from the lower portion of the outer housing and is positioned within the laundry sling.

According to some implementations of the present disclosure, a system for sanitizing a laundry sling that is moveable along one or more support rails includes a bracket, a sanitizing lamp, and an actuator. The bracket is coupled to the one or more support rails such that the bracket is pivotal relative to the one or more support rails between a first position and a second position. The sanitizing lamp is coupled to the bracket such that pivoting of the bracket from the first position to the second position causes a corresponding movement of the sanitizing lamp. The actuator is coupled to the bracket and configured to cause the bracket to pivot from the first position to the second position such that at least a portion of the sanitizing lamp is positioned within the laundry sling.

According to some implementations of the present disclosure, a system for sanitizing a laundry sling that is moveable along a pair of support rails includes a bracket, a sanitizing lamp, a first actuator, a stopper, and a second actuator. The bracket is coupled to the pair of support rails such that the bracket is pivotal relative to the pair of support rails between a first position and a second position. The sanitizing lamp is configured to emit a sanitizing wavelength. The first actuator is coupled to the sanitizing lamp and the bracket such that pivoting of the bracket from the first position to the second position causes a corresponding movement of the first actuator and the sanitizing lamp. The first actuator being configured to move the sanitizing lamp relative to the bracket between a retracted position and an extended position. The stopper is coupled to one of the pair of support rails and is configured to inhibit movement of the laundry sling along the pair of support rails and position the laundry sling generally adjacent to the bracket. The second actuator is coupled to the bracket and is configured to cause the bracket to pivot from the first position to the second position such that at least a portion of the sanitizing lamp is positioned within the laundry sling.

In some implementations of the present disclosure, a method for sanitizing a laundry sling includes moving the laundry sling along one or more support rails, engaging the laundry sling with a stopper such that the laundry sling is generally adjacent to a sanitizing system, pivoting a bracket of the sanitizing system from a first position to a second position such that at least a distal end of a sanitizing lamp coupled to the bracket is positioned within the laundry sling, and emitting, from the sanitizing lamp, a sanitizing wavelength of light for a predetermined sanitizing period.

The above summary of the present disclosure is not intended to represent each embodiment, or every aspect, of the present disclosure. Additional features and benefits of the present disclosure are apparent from the detailed description and figures set forth below.

Figure 1:
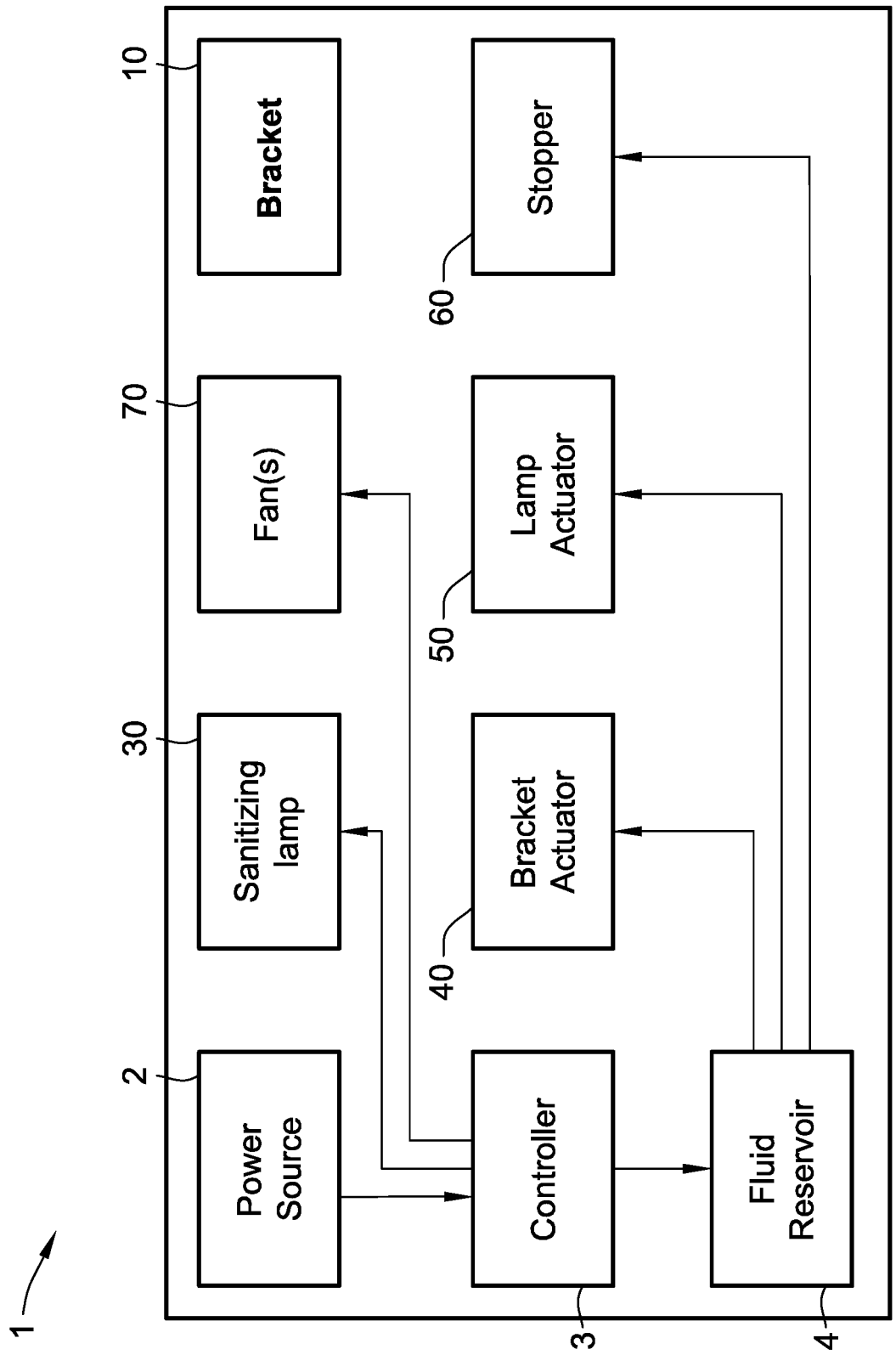
FIG. 1 is a schematic illustration of a sanitizing system according to some implementations of the present disclosure.

While the disclosure is susceptible to various modifications and alternative forms, specific embodiments are shown by way of example in the drawings and are described in detail herein. It should be understood, however, that the disclosure is not intended to be limited to the particular forms disclosed. Rather, the disclosure is to cover all modifications, equivalents and alternatives falling within the spirit and scope of the disclosure.

DETAILED DESCRIPTION

Referring to FIG. 1, a sanitizing system 1 includes a power source 2, a controller 3, a fluid reservoir 4, a bracket 10, a sanitizing lamp 30, a bracket actuator 40, a lamp actuator 50, an optional stopper 60, and optional fan(s) 70. Generally, the sanitizing system 1 is coupled to a laundry transport system (e.g., laundry transport system 100 shown in FIG. 2) and is used for sanitizing a laundry sling suspended from the laundry transport system.

The controller 3 is electrically coupled to the power source 2 and includes one or more processors and an associated memory device for storing instructions that are executable by the one or more processors. The controller 3 also includes a communication module that is communicatively coupled (e.g., by a wireless connection and/or a wired connection) to the fluid reservoir 4, the sanitizing lamp 30, and the optional fan(s) 70. The controller 3 provides power from the power supply 2 to control operation the sanitizing lamp 30 and/or the optional fan(s) 70. Alternatively, the sanitizing lamp 30 and/or the optional fan(s) 70 can be electrically coupled directly to the power source 2 or different power source(s).

The fluid reservoir 4 contains a fluid, such as, for example, compressed air, hydraulic fluid (e.g., oil), or the like. The fluid stored in the fluid reservoir 4 can travel to the bracket actuator 10, the lamp actuator 50, and/or the optional stopper 60 via a connection tube (not shown), such as a flexible hose made from a polymer material, a rigid pipe made from a metal and/or polymer material, or the like, or any combination thereof. As described herein, each of the bracket actuator 10, the lamp actuator 50, and the optional stopper 60 include a pneumatic cylinder which generally includes a piston housing (not shown), a piston (not shown), and a spring (not shown). The piston is disposed within and moveable relative to the piston housing between a retracted position and an extended position. The spring is disposed within the piston housing and generally urges the piston to remain in the retracted position. The controller 3 causes the fluid in the fluid reservoir 4 to be forced into each of the piston cylinders (e.g., by opening a valve) in order to move each of the pistons of the bracket actuator 10, the lamp actuator 50, and/or the optional stopper 60 between a retracted position and an extended position. To move each of the pistons back to the retracted position, the controller 3 stops the flow of fluid from the fluid reservoir 4 (e.g., by closing a valve). In this manner, the controller 3 can be used to control the operation of each of the various components of the sanitizing system 1 described herein. The controller 3 can also include a human-machine interface (e.g., a visual display, a touchscreen display, or the like) that allows a human operator to manually control and/or adjust the operation of the various components of the sanitizing system 1.

The bracket 10 is coupled to the bracket actuator 40, the lamp actuator 50, and optional fan(s) 70. The sanitizing lamp 30 is coupled to the lamp actuator 50 such that the piston of the lamp actuator 50 can move the sanitizing lamp 30 between a retracted position and an extended position relative to the bracket 10. When powered by the power source 2 and/or the controller 3, the sanitizing lamp 30 emits a sanitizing wavelength of length of light for sanitizing nearby surfaces. For example, as described herein, the sanitizing wavelength of light can be a wavelength between about 180 nm and about 260 nm.

The sanitizing system 1 can be coupled to a laundry transport system and generally be used to sanitize a laundry sling suspended from the one or more support rails. In some implementations, operation of the sanitizing system 1 begins with the controller 3 causing the optional stopper 60 to actuate, thereby preventing a laundry sling from moving further along one or more support rails of the laundry transport system. Specifically, the laundry sling is stopped adjacent to (i.e., directly below) the bracket 10. The controller 3 then causes the bracket actuator 40 to pivot the bracket 10 from a first position to a second position relative to the one or more support rails such that the sanitizing lamp 30 is generally vertical (i.e., perpendicular) relative to the one or more support rails. With the bracket 10 in the second position, the controller 3 causes the lamp actuator 50 to move the sanitizing lamp 30 to the extended position such that a distal end of the sanitizing lamp 30 extends into the laundry sling (e.g., a predetermined distance). The controller 3 then causes the sanitizing lamp 30 to emit a sanitizing wavelength of light to sanitize an interior surface of the laundry sling. It is contemplated that the sanitizing lamp 30 can include any number of lamps, each emitting the same and/or different wavelengths of light (e.g., one emits UV light, one emits IR light, one emits visible light, etc., or any combination thereof).

While the sanitizing system 1 is shown as including all of the components described above, more or fewer components can be included in a sanitizing system. For example, an alternative sanitizing system (not shown) includes the power source 2, the controller 3, the fluid reservoir 4, the bracket 10, the sanitizing lamp 30 and the lamp actuator 50. Thus, various sanitizing systems can be formed using any portion of the basic components described herein.

Figure 2:
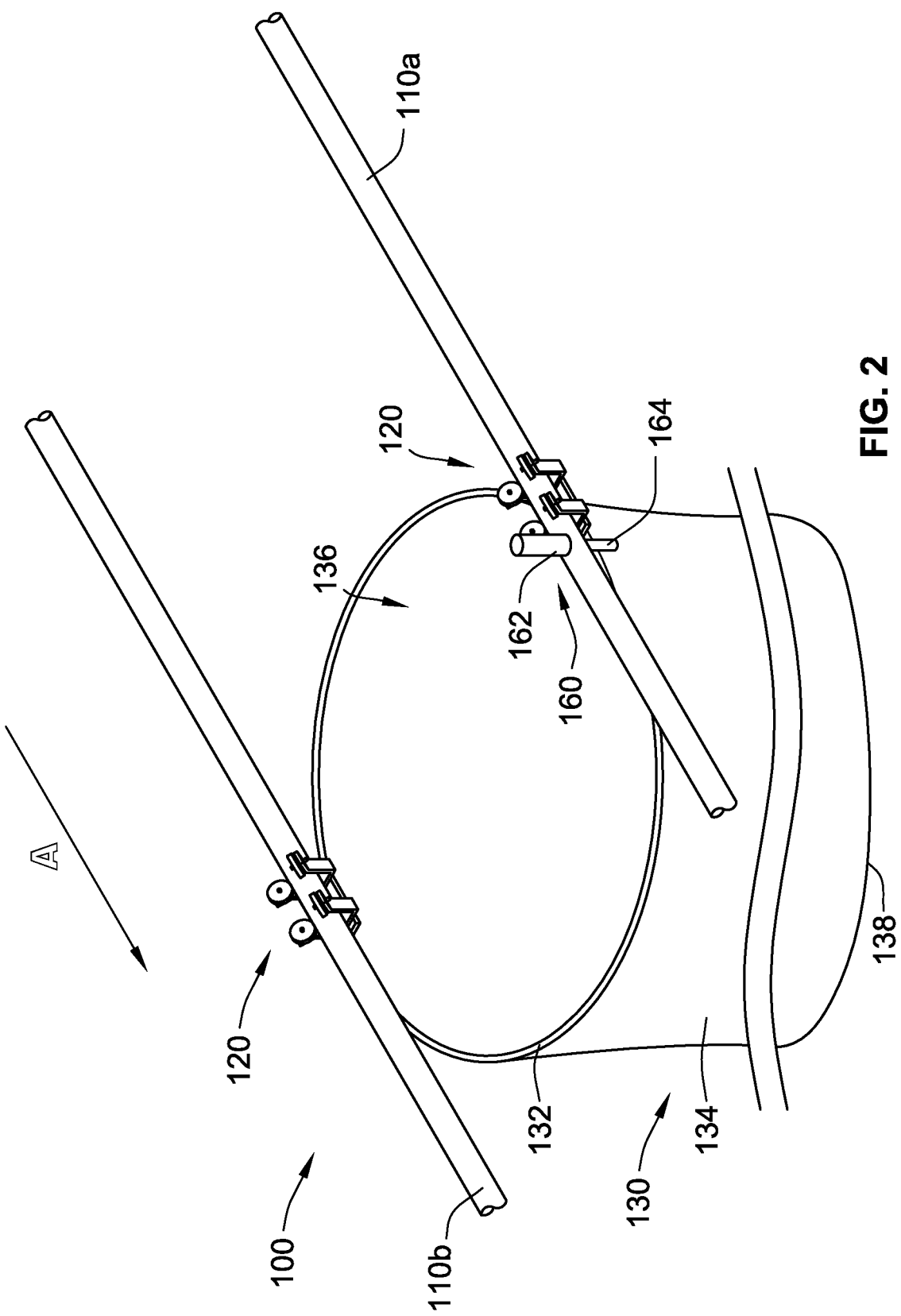
FIG. 2 is a perspective view of an exemplary laundry transport system according to some implementations of the present disclosure.

Referring to FIG. 2, an exemplary laundry transport system 100 includes a first support rail 110a, a second support rail 110b, a plurality of trolleys 120, and a laundry sling 130. Generally, the laundry transport system 100 is used to transport laundry slings (e.g., the laundry sling 130) or bags or hoppers containing laundry between a first location and a second location in a laundry facility. For example, the laundry transport system 100 can be used to transport laundry (i) from delivery trucks to sorters and/or tunnel washers, (ii) from washers to dryers, (iii) from dryers to sorters and/or folders, or the like.

As shown, the first support rail 110a and the second support rail 110b each have a generally cylindrical configuration and extend parallel to one another. While not shown in the drawings, the first support rail 110a and the second support rail 110b are suspended from a ceiling of a structure and/or another support structure which is itself coupled to or suspended from the ceiling (e.g., an I-beam, another support rail, or the like). The first support rail 110a and the second support rail 110b are suspended from the ceiling and/or other support structure such that they are generally sloped relative to horizontal and/or the ceiling and/or another support structure by an angle (e.g., about one degree, about two degrees, about five degrees, about ten degrees, about twenty degrees, etc. or any other suitable angle). The first support rail 110a and the second support rail 110b can be made from a metal material (e.g., aluminum, stainless steel, or the like), a polymer material, or any other suitable material, or any combination thereof. As shown, the first support rail 110a and the second support rail 110b each have a generally cylindrical configuration, although other configurations are possible (e.g., a rectangular configuration, an "I-beam" configuration, a triangular configuration, a polygonal configuration, or the like).

Figure 3A:
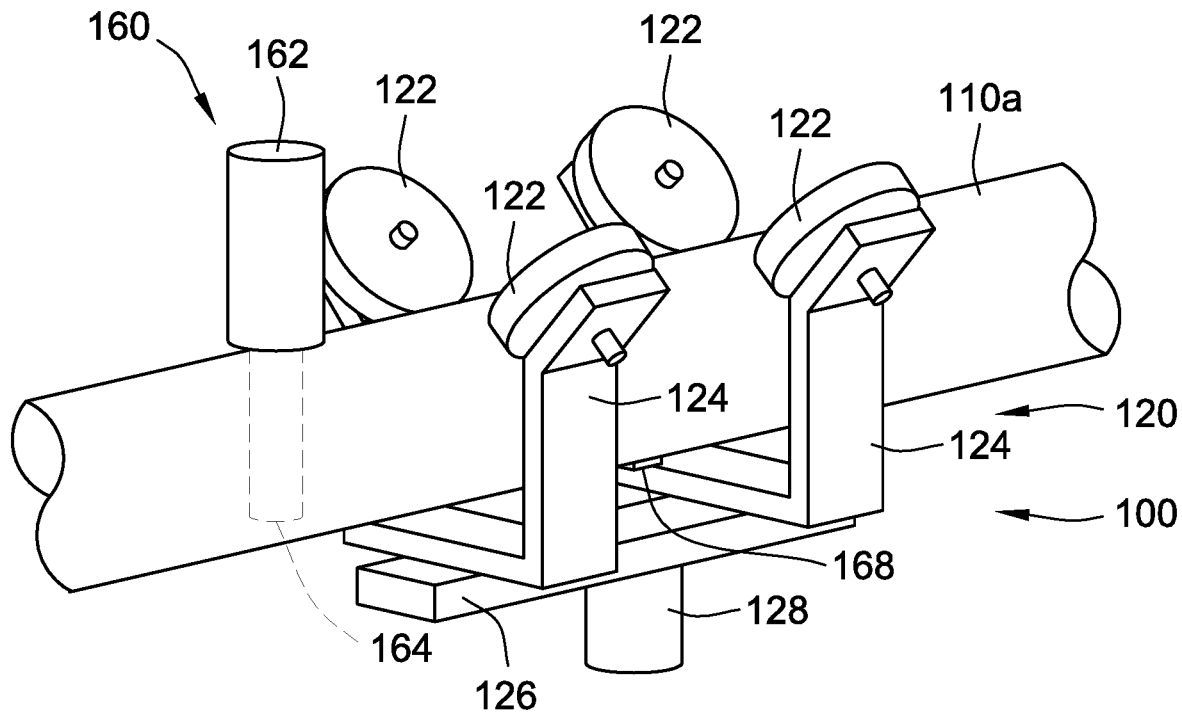
FIG. 3A is an enlarged perspective view of a stopper of the laundry transport system of FIG. 2 in a retracted position according to some implementations of the present disclosure.
Figure 3B:
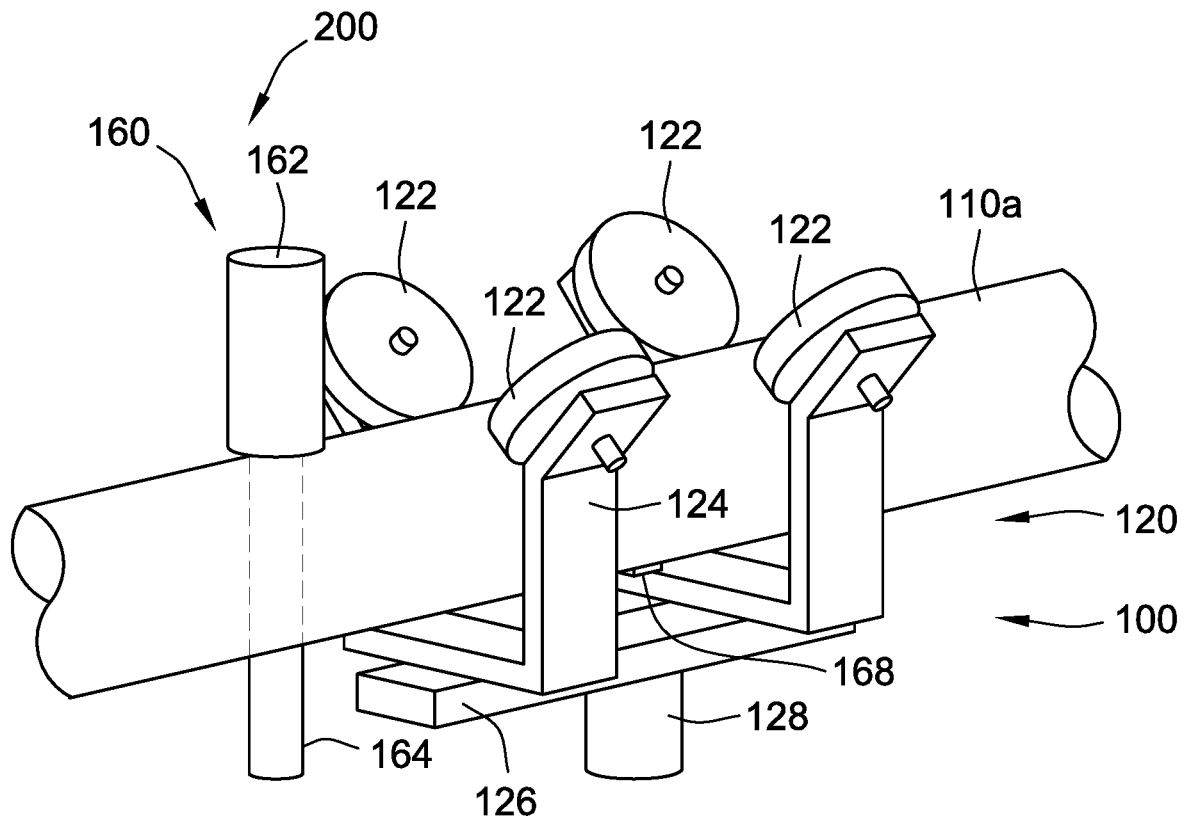
FIG. 3B is an enlarged perspective view of the stopper of the laundry transport system of FIGS. 2 and 3A in an extended position according to some implementations of the present disclosure.

As best shown in FIGS. 3A and 3B, each of the plurality of trolleys 120 is coupled to the first support rail 110a or the second support rail 110b and includes a plurality of wheels 122, a pair of body portions 124, a support bracket 126, and a clasp 128. As shown in FIG. 2, a first pair of the plurality of trolleys 120 is coupled to the first support rail 110a and a second pair of the plurality of trolleys 120 is coupled to the second support rail 110b. The pair of body portions 124 of each of the plurality of trolleys 120 (FIGS. 3A and 3B) is generally sized and shaped such the first support rail 110a and/or second support rail 110b can extend through the body portion 124. Two of the plurality of wheels 122 are coupled to each body portion 124 and are orientated such that each of the plurality of trolleys 120 are moveable along the first support rail 110a and/or the second support rail 110b. Each of the pair of body portions 124 is coupled to one another via the support bracket 126, which in turn is coupled to the clasp 128. As described above, the first support rail 110a and the second support rail 110b are generally sloped, and thus movement of the plurality of trolleys 120 along the first and second support rails 110a, 110b is automatically driven by gravity in the direction of arrow A (FIG. 2). While the plurality of trolleys 120 is shown in FIG. 2 as including two trolleys (i.e., one on the first support rail 110a and one on the second support rail 110b), any number of trolleys is possible (e.g., one trolley, three trolleys, six trolleys, ten trolleys, etc.).

Referring to FIG. 2, the laundry sling 130 includes a support ring 132 (e.g., a rigid support ring), a body portion 134, and a closed bottom 138. The laundry sling 130 is generally used to store and transport laundry (i.e., clothes, linens, fabric, or the like, or any combination thereof). The support ring 132 is coupled to the body portion 134 and maintains the generally cylindrical shape of the laundry sling 130 and defines an upper opening 136. Laundry can be loaded into the laundry sling 130 through the upper opening 136 and the closed bottom 138 prevents the laundry from falling out of the laundry sling 130. The closed bottom 138 can be selectively opened (e.g., by using a drawstring or other similar mechanism) in order to remove the laundry from the laundry sling 130. The body portion 136 of the laundry sling 130 can be made from a flexible material, such as, for example, a fabric material, a canvas material, a polymer material (e.g., nylon), or the like.

The laundry sling 130 is coupled to the first and second support rails 110a, 110b via the plurality of trolleys 120. More specifically, in order to couple the laundry sling 130 to the first and second support rails 110a, 110b, the clasp 128 of a first one of the plurality of trolleys 120 is coupled to a first location on the laundry sling 130, which is in turn suspended from the first support rail 110a by the plurality of wheels 122 (FIGS. 3A and 3B). Similarly, the clasp 128 of a second one of the plurality of trolleys 120 is coupled to a second opposing location on the laundry sling 130 such that the laundry sling 130 is suspended from the first and second support rails 110a, 110b, as best shown in FIG. 2.

Referring back to FIGS. 3A and 3B, the laundry transport system 110 includes an optional stopper 160 and a sensor 168 coupled to the first support rail 110a. The optional stopper 160 is the same as, or similar to, the optional stopper 60 described above in reference to FIG. 1. The optional stopper 160 includes a piston housing 162, a piston 164, and a spring (not shown) disposed in the piston housing 162. As described above, the optional stopper 160 is coupled to a fluid reservoir (not shown) that is the same as, or similar to, the fluid reservoir 4, which in turn is communicatively coupled to a controller (not shown) that is the same as, or similar to, the controller 3. When fluid from the fluid reservoir is forced into the piston housing 162 (e.g., when the controller opens a valve), pressure from the fluid entering the piston housing 162 moves the piston 164 relative to the piston housing 162 by compressing the spring (not shown). Thus, the fluid causes the piston rod 164 to move between a retracted position (FIG. 3A) and an extended position (FIG. 3B).

The sensor 168 is generally used to determine a position of the laundry sling 130 along the first and second support rails 110a, 110b. The sensor 168 can be a motion detecting sensor, an optical sensor, a magnetic sensor, a proximity sensor, or the like, or any combination thereof. When the sensor 168 determines that the laundry sling 130 is positioned below the sensor 168, the sensor 168 causes the controller to move the piston 164 to the extended position (FIG. 3B) to stop further movement of the plurality of trolleys 120 and the laundry sling 130 in the direction of arrow A (FIG. 2). To resume movement of the laundry sling 130 along the first and second support rails 110a, 110b, the controller stops the flow of fluid from the fluid reservoir into the piston housing 162, which causes the spring (not shown) to move the piston 164 back to the retracted position (FIG. 3A).

Although the laundry transport system 100 has been described and illustrated as including a single laundry sling, the laundry transport system 100 can include a plurality of laundry slings that are the same as, or similar to, the laundry sling 130 (i.e., two laundry slings, ten laundry slings, etc.). In such implementations, each of the plurality of laundry slings can be spaced along the first and second support rails 110a, 110b and move in the same or similar manner as the laundry sling 130 as described above (i.e., via the plurality of trolleys 120).

Further, while the laundry transport system 100 has been described and illustrated as having two support rails (i.e., the first support rail 110a and the second support rail 110b), in some implementations, the laundry transport system 100 can include a single support rail that is the same as, or similar to, the first support rail 110a and/or the second support rail 110b. In such implementations, the laundry sling 130 is moveable along the single support rail in the same or similar manner as described above with respect to the first support rail 110a and the second support rail 110b (i.e., a plurality of trolleys that are the same as, or similar to, the plurality of trolleys 120, or the like). In other implementations, the laundry transport system 100 can include more than two support rails (e.g., three rails, four rails, etc.).

Figure 4A:
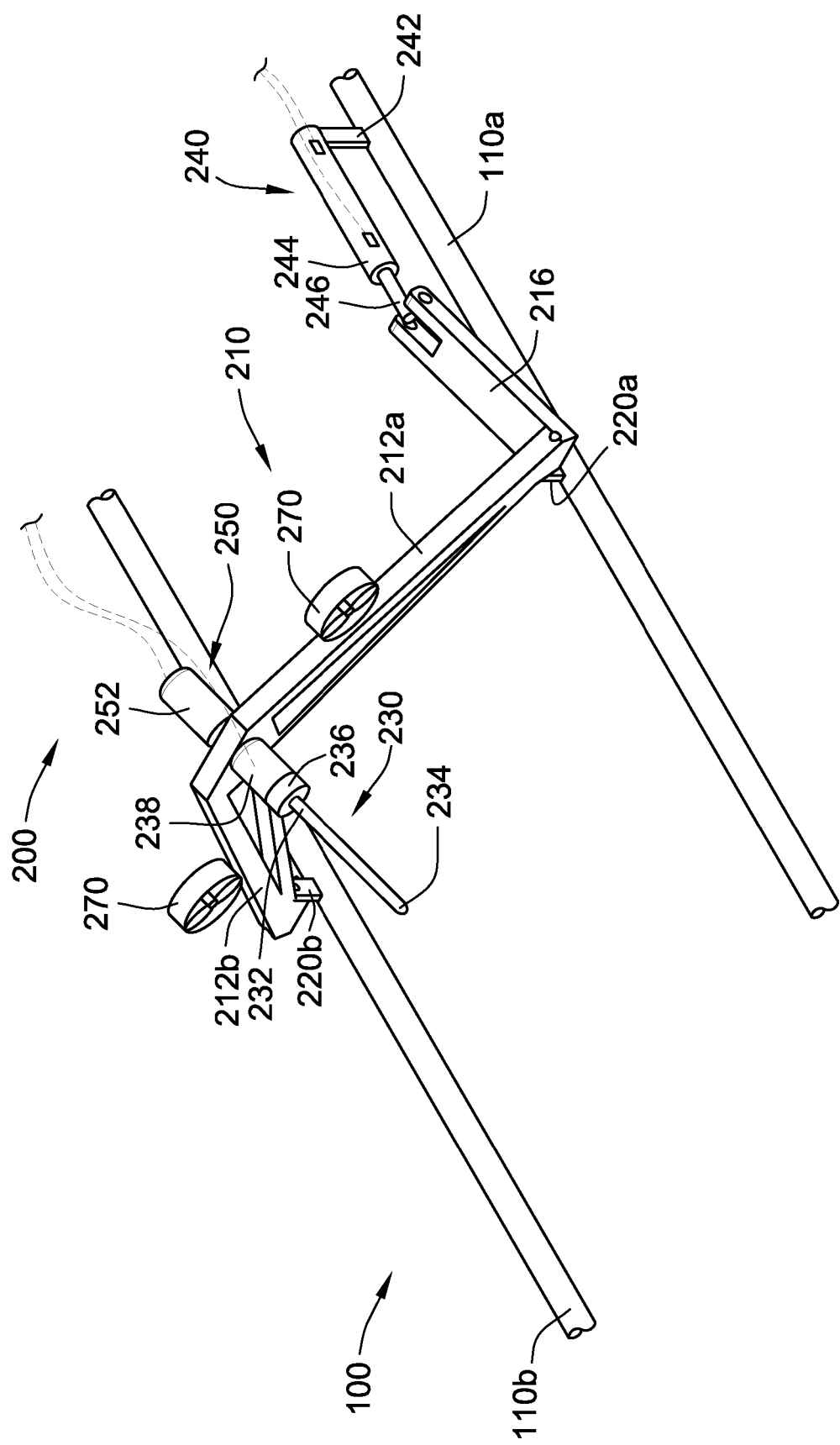
FIG. 4A is a perspective view of a sanitizing system according to some implementations of the present disclosure.
Figure 4B:
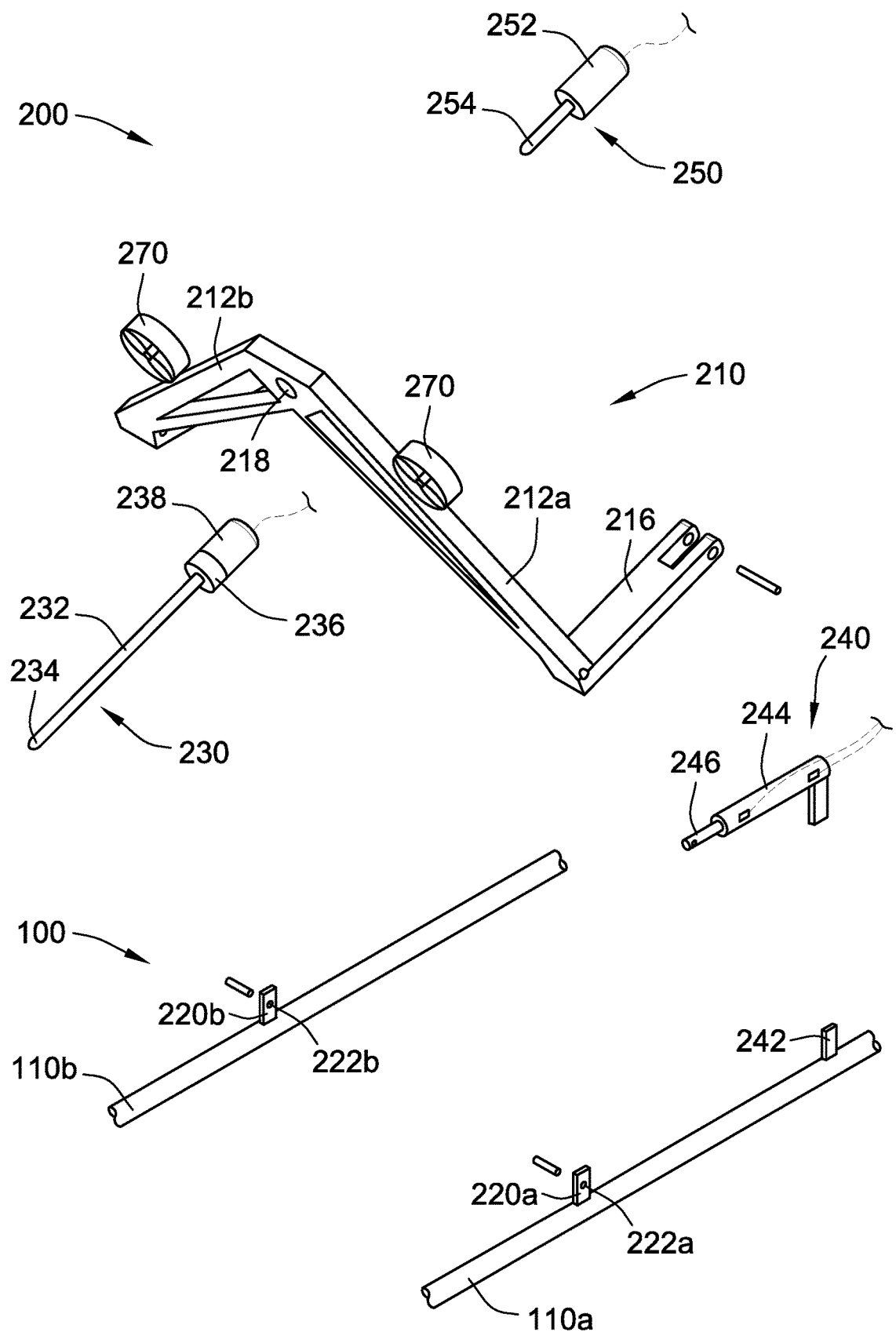
FIG. 4B is an exploded view of the sanitizing system of FIG. 4A according to some implementations of the present disclosure.

Referring generally to FIGS. 4A and 4B, a sanitizing system 200, that is the same as, or similar to, the sanitizing system 1, includes a bracket 210, a sanitizing lamp 230, a bracket actuator 240, an optional lamp actuator 250, and an optional plurality of fans 270. The sanitizing system 200 is generally used for sanitizing the laundry sling 130 of the laundry transport system 100. More specifically, the bracket actuator 240 causes the bracket 210 to pivot such that (i) at least a portion of the sanitizing lamp 230 is positioned within the laundry sling 130 and (ii) the sanitizing lamp 230 provides a sanitizing wavelength of light to substantially sterilize an interior surface of the laundry sling 130.

The sanitizing system 200 also includes a power supply (not shown) that is the same as, or similar to, the power supply 2 (FIG. 1), a controller (not shown) that is the same as, or similar to, the controller 3 (FIG. 1), and a fluid reservoir (not shown) that is the same as, or similar to, the fluid reservoir 4 (FIG. 1). The controller automatically controls the operation of the various components of the sanitizing system 200 in the same, or similar, manner as the controller 3 described above.

The bracket 210 includes a first support arm 212a, a second support arm 212b, a pivoting arm 216, and a generally central aperture 218. As shown, the first support arm 212a, the second support arm 212b, and the pivoting arm 216 are coupled to one another and are unitary and/or a monolithic component. However, other mechanisms for coupling the first support arm 212a, the second support arm 212b, and the pivoting arm 216 are possible, such as, for example, a welded connection, an adhesive connection, a pin and aperture system, locking tabs, or the like, or any combination thereof. Further, each of the first support arm 212a, the second support arm 212b, and the pivoting arm 216 can be made from a metal material, a polymer material, or the like, or any combination thereof.

As best shown in FIG. 4A, the first support arm 212a is coupled to a first mounting post 220a, which is in turn coupled to the first support rail 110a (best shown in FIG. 4B). Due to the orientation of the plurality of wheels 122 of each of the plurality of trolleys 120 (FIGS. 3A and 3B), the plurality of trolleys 120 can move along the first support rail 110a without being inhibited by (i.e., contacting) the first mounting post 220a and/or the first support arm 212a of the bracket 210. The first mounting post 220a can be coupled to the first support rail 110a by various mechanisms, including, for example, a welded connection, a fastener (e.g., a bolt, a pin, or the like), a locking collar, or the like, or any combination thereof. The first support arm 212a of the bracket 210 is coupled to the first mounting post 220a at a first pivot point 222a such that the first support arm 212a is pivotable about the first pivot point 222a relative to the first support rail 110a (i.e., the bracket 210 can rotate relative to the first and second support rails 110a, 110b about the pivot point 222a).

The second support arm 212b of the bracket 210 is coupled to a second mounting post 220b in the same, or similar, manner as the first support arm 212a and first mounting post 220a described above. The second mounting post 220b is coupled to the second support rail 110b such that the plurality of trolleys 120 can move along the second support rail 110b without being inhibited by the second mounting post 220b and/or the second support arm 212b of the bracket 210. The second mounting post 220b can be coupled to the second support rail 110b by various mechanisms, including, for example, a welded connection, a fastener (e.g., a bolt, a pin, or the like), a locking collar, or the like, or any combination thereof. The second support arm 212b of the bracket 210 is coupled to the second mounting post 220b at a second pivot point 222b such that the second support arm 212b is pivotable about the second pivot point 222b relative to the second support rail 110b. Thus, the entire bracket 210 is pivotable about the first and second pivot points 222a, 222b relative to the first and second support rails 110a, 110b.

As shown in FIGS. 4A and 4B, the pivoting arm 216 is coupled to and extends from the first support arm 212a and the first pivot point 222a. Like the first support arm 212a, the pivoting arm 216 is pivotable about the first pivot point 222a relative to the first support rail 110a. As described above, because the pivoting arm 216, the first support arm 212a, and the second support arm 212b are all coupled to one another, movement of any one the first support arm 212, the second support arm 212b, and/or the pivoting arm 216 causes a corresponding movement of the others. Thus, pivoting of the pivoting arm 216 about the first pivot point 222a causes the first support arm 212a and the second support arm 212b to pivot (i.e., rotate) about the first pivot point 222a and the second pivot point 222b, respectively.

The sanitizing lamp 230 includes a proximal end 232 and a distal end 234. The proximal end 232 of the sanitizing lamp 230 is coupled to a socket 236, which is electrically coupled to a ballast 238. The ballast 238 is electrically coupled to a power source (e.g., power source 2) and/or a controller (e.g., controller 3). The ballast 238 is an electronic circuit that acts as a transformer and regulates power delivered from the power supply (not shown) to the sanitizing lamp 230. Thus, the ballast 238 can provide a desired start-up voltage for the sanitizing lamp 230 and/or maintain a uniform current when the sanitizing lamp 230 is operating.

As best shown in FIG. 4A, the optional lamp actuator 250, which is the same as, or similar to, the lamp actuator 50 described above, is coupled to the bracket 210 on an opposing side relative to the socket 236 and the ballast 238. The optional lamp actuator 250 includes a piston cylinder 252, a piston 254 (FIG. 4B), and a spring (not shown) disposed within the piston cylinder 252. The optional lamp actuator 250 is also coupled to a fluid reservoir (e.g., fluid reservoir 4) and operates in the same, or similar, manner as the optional stopper 160 described above (i.e., a controller causes fluid from the fluid reservoir to enter the piston cylinder 252, compress the spring, and extend the piston 254 relative to the piston cylinder 252). The piston 254 extends through the central aperture 218 (FIG. 4B) and is rigidly coupled to the ballast 238. Thus, movement of the piston 254 causes a corresponding movement of the ballast 238, the socket 236, and the sanitizing lamp 230. Further, because the optional lamp actuator 250 is coupled to the bracket 210, pivoting of the bracket 210 causes a corresponding movement of the optional lamp actuator 250 and the sanitizing lamp 230.

In some implementations, the sanitizing system 200 does not include the optional lamp actuator 250. In such implementations, the ballast 238 is coupled to the bracket 210 and the socket 236 is disposed within the generally central aperture 218 of the bracket 210 and is coupled to both the ballast 238 and the sanitizing lamp 230. In such implementations, pivoting of the bracket 210 about the first and second pivot points 222a, 222b causes a corresponding movement of the sanitizing lamp 230, the socket 236, and the ballast 238 relative to the first and second support rails 110a, 110b.

As shown, the sanitizing lamp 230 has a generally cylindrical configuration, however, other configurations are possible, such as, for example, a circular configuration, a coiled spiral-like configuration, a generally "U-shaped" configuration, a double tube configuration, a rectangular configuration, a triangular configuration, a polygonal configuration, or the like, or any combination thereof. Further, the sanitizing lamp 230 can optionally include a protective cover (e.g., made from a glass material, a transparent or semi-transparent polymer material, or the like) to aid in protecting the sanitizing lamp 230 from being damaged or shattering.

When supplied power via the ballast 238, the sanitizing lamp 230 emits a sanitizing wavelength of light. The sanitizing wavelength of light disinfects and sterilizes surfaces by killing or inactivating microorganisms (e.g., bacteria, viruses, fungi, or the like). The sanitizing wavelength of light emitted by the sanitizing lamp 230 can range between about 10 nm and 400 nm, between about 315 nm and about 400 nm (a range that is commonly referred to as "black light" or "UVA" light), between about 280 nm and about 315 nm (a range that is commonly referred to as "UVB" light) and/or between about 100 nm and about 260 nm (a range that is commonly referred to as "UVC" light). As described herein, the sanitizing wavelength of light is preferably between about 187 nm and about 254 nm. In some implementations, the sanitizing wavelength of light is about 187 nm. In some implementations, the sanitizing wavelength of light is about 254 nm.

When the sanitizing wavelength of light emitted by the sanitizing lamp 230 is about 187 nm, the sanitizing wavelength of light produces a volume of o-zone gas. More specifically, the sanitizing wavelength of light emitted by the sanitizing lamp 230 reacts with ambient air around the sanitizing lamp 230 and within the laundry sling 130 and breaks down oxygen molecules ($O_2$) into oxygen atoms (O). These oxygen atoms then react with other oxygen ($O_2$) molecules in the ambient air to form o-zone gas ($O_3$ molecules). O-zone gas acts as a powerful disinfectant, oxidant, and/or deodorizer. O-zone gas disinfects by killing and/or inactivating microorganisms, and can be many times more effective than chemicals (e.g., chlorine). Because of its high oxidation potential, o-zone gas can precipitate a variety of organic and inorganic contaminates, including, for example, iron, manganese, sulfides, metals, body oils, sweat, and saliva. Further, o-zone gas oxidizes organic chemicals that are responsible for producing unwanted odors.

When the sanitizing wavelength of light emitted by the sanitizing lamp 230 is about 254 nm, a wavelength that is commonly referred to as "germicidal ultra-violet ("UV") light", the sanitizing wavelength of light kills and/or inactivates microorganisms. When a volume of o-zone gas is present in the ambient air surrounding the sanitizing lamp 230 (e.g., subsequent to the production of o-zone gas via a sanitizing wavelength of light that is about 187 nm), the sanitizing wavelength of light, which is about 254 nm, converts o-zone gas ($O_3$) to hydroxyl radicals (*OH). Hydroxyl radicals are often referred to as the "detergent" of the troposphere because they react with many pollutants, decomposing them through a process known as "cracking". The hydroxyl radicals kill and/or inactivate microorganism and sanitize adjacent surfaces.

In some implementations, the sanitizing lamp 230 can selectively emit any one of a plurality of sanitizing wavelengths of light. In such implementations, the sanitizing wavelength of light emitted by the sanitizing lamp 230 can be adjusted within a range of wavelengths (i.e., a between a wavelength of about 180 nm and a wavelength of about 260 nm). In this manner, the sanitizing wavelength of light emitted by the sanitizing lamp 230 can adjusted to about 187 nm in order to produce o-zone gas, and then subsequently adjusted to about 254 nm in order to emit a germicidal UV light and produce hydroxyl radicals.

Alternatively, rather than including the sanitizing lamp 230 (i.e., a single sanitizing lamp), the sanitizing system 200 can include a plurality of sanitizing lamps that are the same as, or similar to, the sanitizing lamp 230 (e.g., two sanitizing lamps, three sanitizing lamps, six sanitizing lamps, etc.). In such implementations, each of the plurality of sanitizing lamps emits an individual sanitizing wavelength (e.g., a first one of the plurality of sanitizing lamps emits a first sanitizing wavelength of about 187 nm and a second one of the plurality of sanitizing lamps provides a second sanitizing wavelength of about 254 nm). Thus, the plurality of sanitizing lamps can emit a plurality of sanitizing wavelengths sequentially and/or simultaneously. The plurality of sanitizing lamps can be disposed within a protective housing, or can be coupled to the bracket 210 at different locations (i.e., a first one of the plurality of sanitizing lamps is coupled to the first support arm 212a of the bracket 210 and a second one of the plurality of sanitizing lamps is coupled to the second support arm 212b of the bracket 210).

As shown in FIGS. 4A and 4B, the bracket actuator 240 is pivotally coupled to an actuator mounting post 242 and includes a piston housing 244, a piston 246 that is disposed within and moveable with respect to the piston housing 244, and a spring (not shown) disposed within the piston housing 244. The actuator mounting post 242 is coupled to the first support rail 110a in the same, or similar, manner as the first and second mounting posts 220a, 220b described above (i.e., the bracket actuator 240 is coupled to the first support rail 110a such that it does not inhibit movement of the laundry sling 130 along the first and second support rails 110a, 110b). The bracket actuator 240 operates in the same, or similar, manner as the bracket actuator 40 and optional stopper 160 described above (i.e., the bracket actuator 240 is coupled to a fluid reservoir, and pressure from fluid entering the piston housing 244 causes movement of the piston 246 relative to the piston housing 244). The piston rod 246 is coupled to the pivoting arm 216 of the bracket 210 such that movement of the piston rod 246 (e.g., an extension of the piston rod 246 relative to the piston housing 244) causes a pivotal movement of the bracket 210 about pivot points 222a, 222b.

Figure 5A:
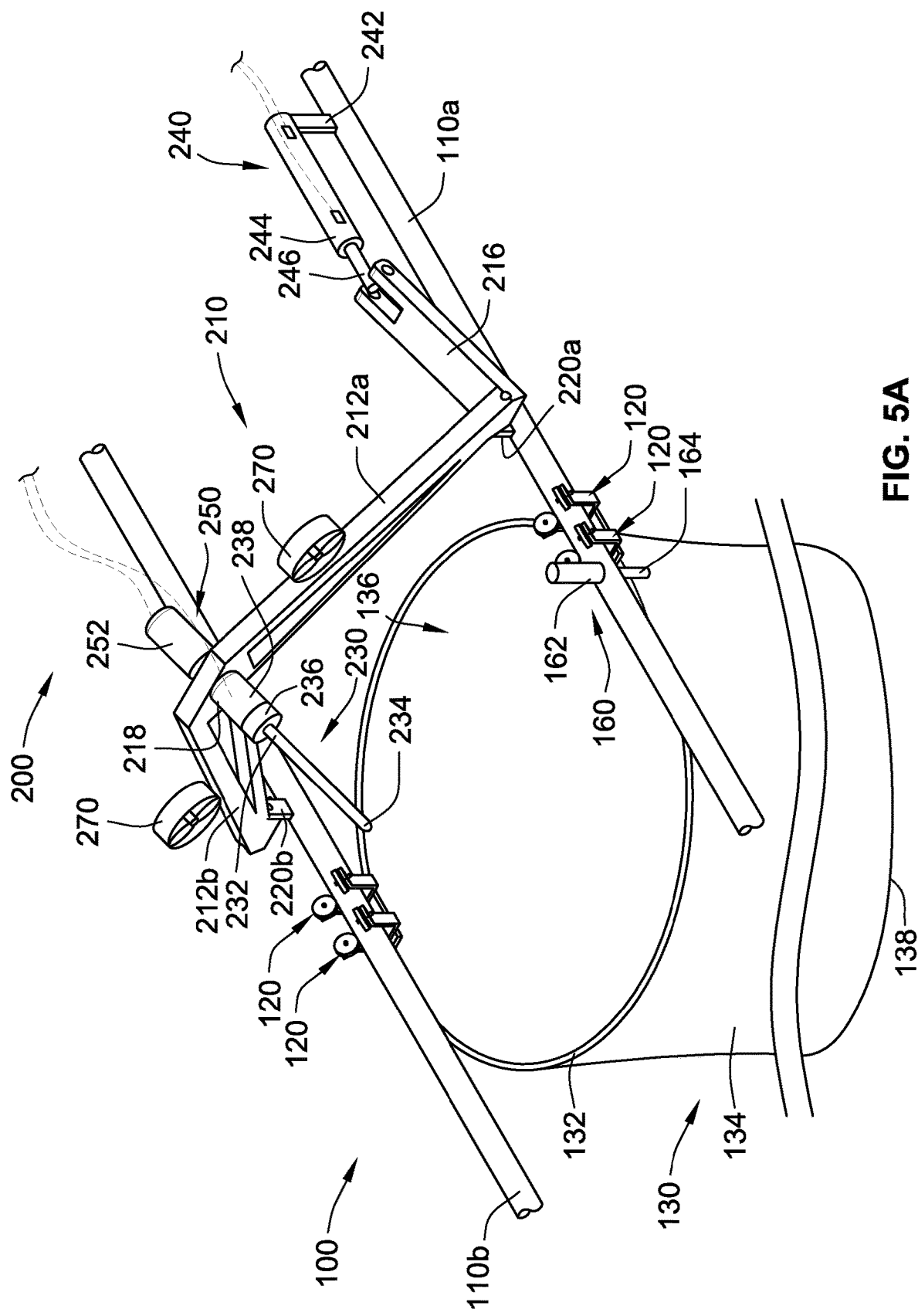
FIG. 5A is a perspective view of the sanitizing system of FIG. 4A coupled to a laundry transport system according to some implementations of the present disclosure.
Figure 5B:
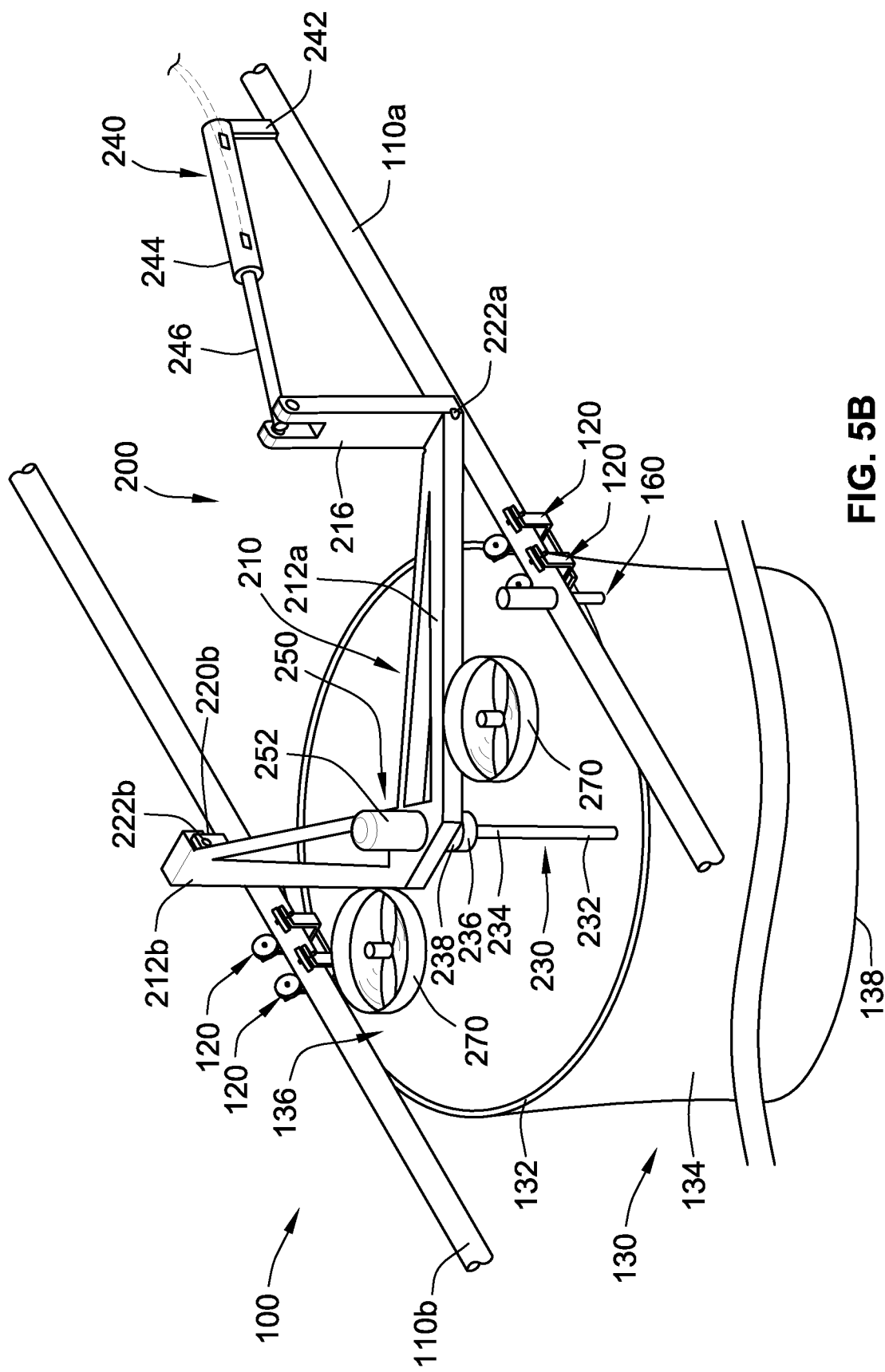
FIG. 5B is a perspective view of the sanitizing system of FIGS. 4A and 5A with a bracket pivoted to a second position according to some implementations of the present disclosure.
Figure 5C:
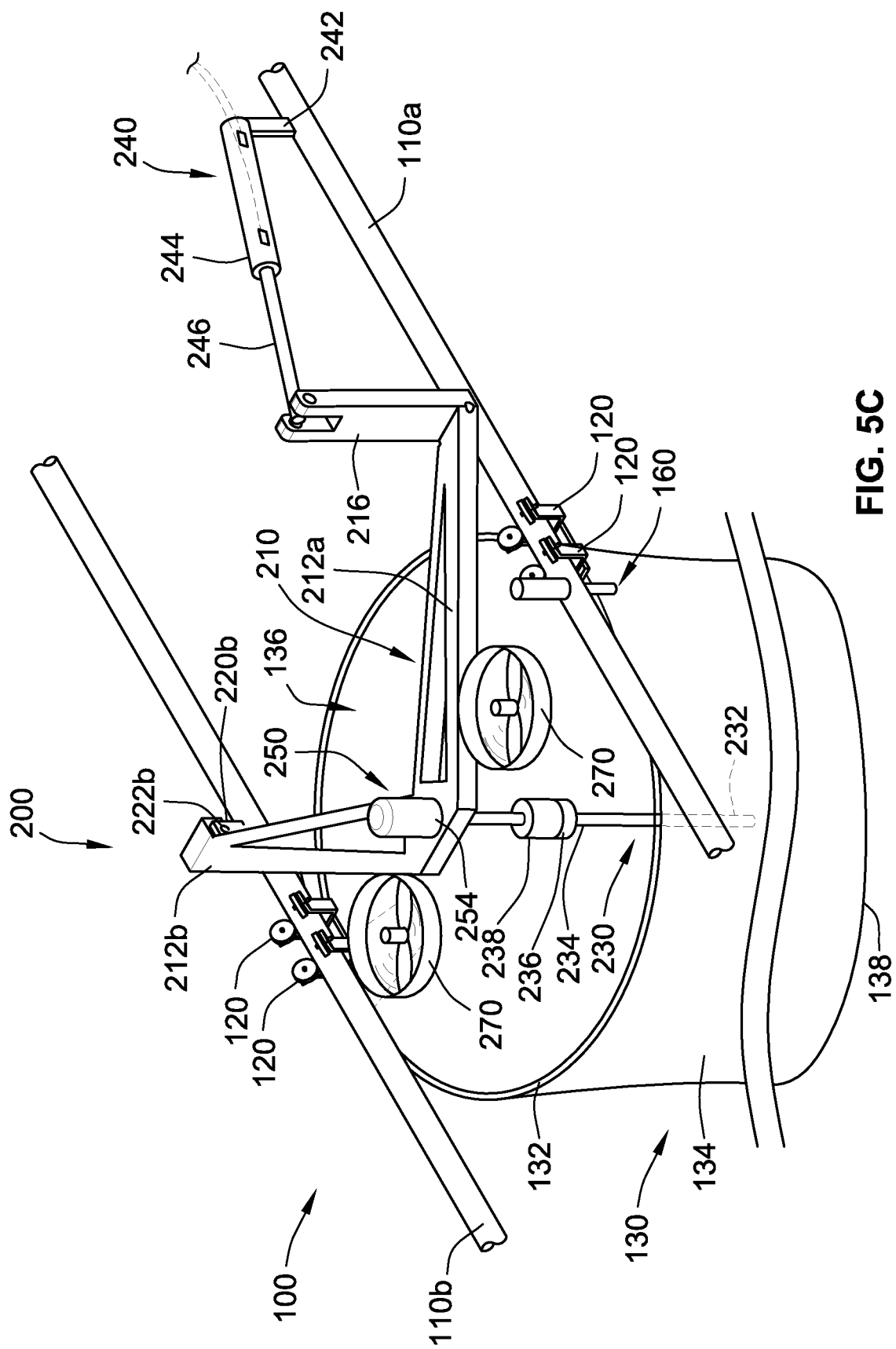
FIG. 5C is a perspective view of the sanitizing system of FIGS. 4A, 5A, and 5B with a sanitizing lamp moved to an extended position according to some implementations of the present disclosure.

Referring to FIGS. 5A-5C, operation of the sanitizing system 200 according to some implementations of the present disclosure is described. As shown in FIG. 5A, the bracket 210 is in a first position (e.g., retracted or home position). In the first position, the bracket 210 is positioned relative to the first and second support rails 110a, 110b such that the distal end 234 of the sanitizing lamp 230 is positioned above the first and second support rails 110a, 110b. Thus, when the bracket 210 is in the first position as shown in FIG. 5A, the laundry sling 130 is free to move along the first and second support rails 110a, 110b without being inhibited by or contacting the bracket 210 or the sanitizing lamp 230.

Further, the laundry sling 130 is positioned below (e.g., generally adjacent to) the bracket 210. To position the laundry sling 130 in this location, the optional stopper 160 is moved to the extended position (FIGS. 3B and 5A) to prevent movement of the plurality of trolleys 120, as described above. For example, the sensor 168 (FIG. 3B) determines that the laundry sling 130 is positioned below the bracket 210 and causes the piston 164 of the stopper 160 to engage at least one of the plurality of trolleys 120 to keep the laundry sling 130 in place.

Referring to FIG. 5B, the bracket 210 is shown in a second position (e.g., extended or operating position). To move the bracket 210 from the first position (FIG. 5A) to the second position (FIG. 5B), the bracket actuator 240 moves the piston 246 from a retracted position (FIG. 5A) to an extended position (FIG. 5B). As the piston 246 moves to the extended position (FIG. 5B), the piston 246 causes the pivoting arm 218 to pivot about the first pivot point 222a, causing the bracket 210 to pivot about the first and second pivot points 222a, 222b relative to the first and second support rails 110a, 110b. As shown, when the bracket 210 is in the second position, the sanitizing lamp 230 is generally vertical (e.g., perpendicular relative to the first and second support rails 110a, 110b). Further, when the bracket is in the second position, at least a portion of the distal end 234 of the sanitizing lamp 230 extends below the first and second support rails 110a, 110b and protrudes through the upper opening 136 of the laundry sling 130.

Figure 6A:
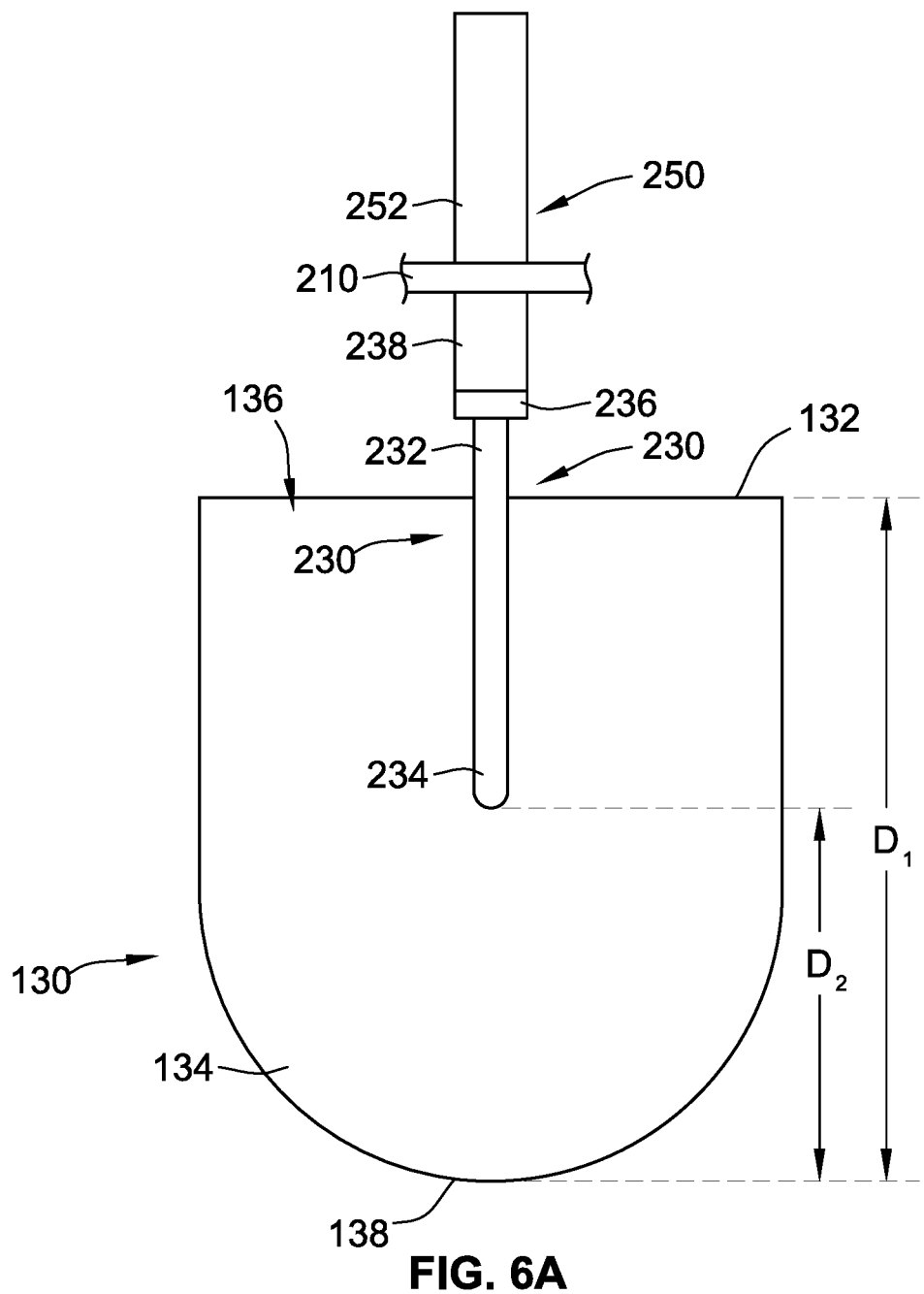
FIG. 6A is a partial side view of the sanitizing system of FIG. 5B with a lamp actuator in a retracted position according to some implementations of the present disclosure.

As shown in FIG. 6A, when the bracket 210 is in the second position and the sanitizing lamp 230 is in a retracted position (FIG. 5B), a tip of the distal end 234 of the sanitizing lamp 230 is positioned at a distance D2 from the closed bottom 138 of the laundry sling 130. A height of the laundry sling 130 is defined by a first distance D1 between the support ring 132 and the closed bottom 138 of the laundry sling 130. In the position shown in FIGS. 5B and 6A, the second distance D2 can be about 80% of the first distance D1, about 60% of the first distance D1, about 50% of the first distance D1, about 40% of the first distance D1, about 30% of the first distance D1, about 20% of the first distance D1, about 10% of the first distance D1, etc. The effectiveness of the sanitizing wavelength of light emitted by the sanitizing lamp 230 in sanitizing the laundry sling 130 is generally a function of the second distance D2. In other words, the distal end 234 of the sanitizing lamp 230 must extend far enough into the upper opening 136 of the laundry sling 130 for the sanitizing wavelength of light to be most effective in sanitizing the entire interior surface of the laundry sling 130.

To reduce the second distance D2 (the distance between the closed bottom 138 and the tip of the distal end 234 of the sanitizing lamp 230), a longer sanitizing lamp can be used (e.g., a sanitizing lamp with an increased distance between its proximal and distal ends). However, when the bracket actuator 240 moves the bracket 210 from first position (FIG. 5A) to the second position (FIG. 5B), the sanitizing lamp 230 must clear the support ring 132 of the laundry sling 130 before the distal end 234 of the sanitizing lamp protrudes into the upper opening 136 of the laundry sling 130. If the sanitizing lamp 230 is too long, the sanitizing lamp 230 may contact/hit the support ring 132 of the laundry sling 130 as the bracket 210 pivots to the second position (FIG. 5B). This would prevent proper operation of the sanitizing system 200 because the distal end 234 of the sanitizing lamp 230 will not be positioned within the laundry sling 130. Further, contact between the sanitizing lamp 230 and support ring 132 during pivoting could cause the sanitizing lamp 230 to break, and broken glass falling into the laundry sling 130 would necessitate a difficult and time consuming process of removing the laundry sling 130 from the first and second support rails 110a, 110b for cleaning. Thus, as shown in FIGS. 5B and 6A, the sanitizing lamp 230 is positioned in a retracted position relative to the bracket 210 to prevent the sanitizing lamp 230 from coming into contact with the laundry sling 130 during pivoting of the bracket 210.

Referring to FIG. 5C, the bracket 210 is in the second position and the sanitizing lamp 230 is in an extended position. To move the sanitizing lamp 230 from a retracted position (FIGS. 5A and 5B) to the extended position (FIG. 5C), the lamp actuator 250 causes movement of the piston 254 (e.g., using fluid as described above), which in turn causes movement of the ballast 238, the socket 236, and the sanitizing lamp 230 relative to the bracket 210. As the piston 254 moves relative to the piston housing 254 of the lamp actuator 250, the piston 254 extends through the central aperture 218 of the bracket 210 (FIG. 4B) and moves the sanitizing lamp 230, the socket 236, and the ballast 238 away from the bracket 210 (e.g., vertically downwards towards the closed bottom 136 of the laundry sling 130).

Figure 6B:
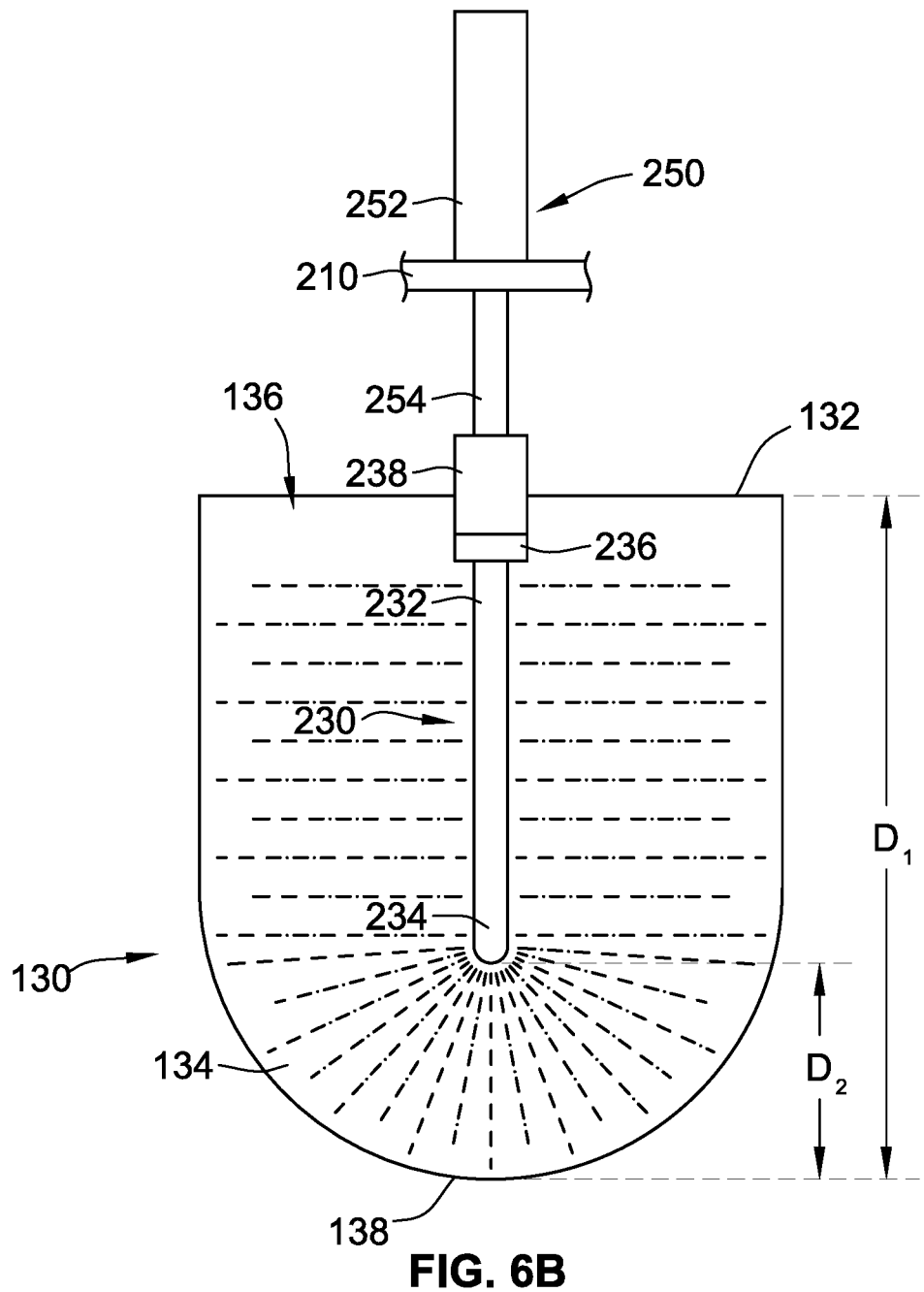
FIG. 6B is a partial side view of the sanitizing system of FIGS. 5C and 6A with the lamp actuator in an extended position according to some implementations of the present disclosure.

Referring to FIG. 6B, when the sanitizing lamp 230 is in the extended position, the second distance D2 (the distance between the tip of the distal end 234 of the sanitizing lamp 230 and the closed bottom 136) is reduced relative to the second distance D2 when the sanitizing lamp 230 is in the retracted position (FIG. 6A). In this manner, the optional lamp actuator 250 can move the sanitizing lamp 230 to the extended position (FIGS. 5C and 6B) such that the second distance D2 is between about 30% of the first distance D1 and about 90% of the first distance D1. For example, when the sanitizing lamp 230 is in the retracted position (FIGS. 5B and 6A), the second distance D2 can be about 10% of the first distance D1, and when the sanitizing lamp 230 is in the extended position (FIGS. 5C and 6B), the second distance D2 can be about 30% of the first distance D1. In this manner, the optional lamp actuator 250 can be used to reduce the distance between the distal end 234 of the sanitizing lamp 230 and the closed bottom 138 of the laundry sling 130, and increase the effectiveness of the sanitizing wavelength of light. Preferably, the second distance D2 is between about 30% of the first distance D1 and about 50% of the first distance D1 to sterilize the interior surface of the laundry sling 130 (or reduce the required sanitizing period to do so).

Subsequent to the bracket actuator 240 moving the bracket 210 to the second position (FIG. 5B), and the optional lamp actuator 250 moving the sanitizing lamp 230 to the extended position (FIG. 5C), the sanitizing lamp 230 provides a sanitizing wavelength of light as described above for a predetermined sanitizing period to sanitize the interior surface of the laundry sling 130. The predetermining sanitizing period can be, for example, between about one second and about one minute, between about five seconds and ten seconds, between about five seconds and about twenty seconds, between about five seconds and fifty seconds, and/or between about five seconds and 110 seconds. The required length of the sanitizing period is generally proportional to the intensity/brightness of the light emitted by the sanitizing lamp 230. For example, a sanitizing lamp emitting a sanitizing wavelength with a relatively low intensity/brightness may require a longer sanitizing period in order to substantially sterilize the interior surface of the laundry sling 130. Other factors affecting the required sanitizing period may include the distance between the sanitizing lamp 230 and the interior surface of the laundry sling 130, the intensity of ambient light in the laundry sling 130, the properties of the ambient air (e.g., the air temperature and/or humidity) and/or the contamination/soil level of the laundry sling 130.

Further, in some implementations, the sanitizing lamp 230 emits a plurality of sanitizing wavelengths of light wavelengths in a predetermined sequence. For example, the predetermined sequence can include emitting a first sanitizing wavelength of light for a first predetermined sanitizing period, and subsequent to the first sanitizing period, emitting a second sanitizing wavelength of light for a second predetermined sanitizing period. As a further example, the first sanitizing wavelength can be about 187 nm (which produces a volume of o-zone gas) and the second sanitizing wavelength of light can be about 254 nm (i.e., a "germicidal UV light"). Because the germicidal UV light is provided immediately subsequent to the production of the volume of o-zone gas, the germicidal UV light reacts with the volume of o-zone gas to produce hydroxyl radicals (*OH), as described above. Thus, the predetermined sequence combines three independent sanitizing mechanisms to sanitize the interior surface of the laundry sling 130: (i) o-zone gas, (ii) germicidal UV light, and (iii) hydroxyl radicals. Further this combination of sanitizing mechanisms can decrease the required length of the first and second predetermined sanitizing periods, increasing the speed and efficiency of the sanitizing system 200.

Subsequent to the sanitizing lamp 230 emitting the sanitizing wavelength of light for the predetermined sanitizing period, the lamp actuator 250 moves the sanitizing lamp 230 from the extended position (FIG. 5C) to the retracted position (FIG. 5B). The bracket actuator 240 then pivots the bracket 210 from the second position (FIG. 5B) to the first position (FIG. 5A). The optional stopper 160 then disengages the laundry sling 130 (e.g., the piston 164 moves to the retracted position) to permit the laundry sling 130 to continue moving along the first and second support rails 110a, 110b (e.g., in the direction of arrow A (FIG. 2)). The sanitizing system 200 is then ready to repeat the operation described above to sanitize a second laundry sling.

The optional plurality of fans 270 is the same as, or similar to, the optional fan(s) 70 (FIG. 1) described above. As shown in FIGS. 4A-5C, each of the optional plurality of fans 270 is coupled to the bracket 210. The optional plurality of fans 270 are generally positioned relative to the sanitizing lamp 230 such that the optional plurality of fans 270 force air past the sanitizing lamp 230 and circulate air within the laundry sling 130 when the laundry sling 130 positioned below the bracket 210 (for example, as shown in FIGS. 5A-5C). More specifically, when the bracket 210 is in the second position (FIG. 5B), the optional plurality of fans 270 are pointed directly at the upper opening 136 of the laundry sling 130. While the optional plurality of fans 270 is shown as including two fans, the optional plurality of fans 270 can include a single fan or more than two fans (e.g., four fans, eight fans, etc.). Further, while each of the optional plurality of fans 270 is shown and described herein as being coupled to the bracket 210, the optional plurality of fans 270 can also be coupled to, for example, the first support rail 110*a*, the second support rail 110*b*, or otherwise positioned above the laundry sling 130 and/or the sanitizing lamp 230.

As described above, the body portion 134 of the laundry sling 130 is generally made from a flexible material (e.g., a canvas material). While the support ring 132 generally maintains the overall shape of the laundry sling 130, the body portion 134 of the laundry sling 130 often has folds, wrinkles, creases, or the like, which may inhibit the sanitizing wavelength of light emitted by the sanitizing lamp 230 from reaching portions of the interior surface of the laundry sling 130. As described herein, the sanitizing wavelength emitted by the sanitizing lamp 230 can be about 187 nm in order to produce a volume of o-zone gas. When the bracket 210 is in the second position (FIG. 5B) and/or the sanitizing lamp 230 is also in the extended position (FIG. 5C), o-zone gas produced by the sanitizing lamp 230 permeates throughout the interior of the laundry sling 130, including between the folds, wrinkles, creases, or the like. Thus, the o-zone gas sterilizes the areas of the body portion 134 of the laundry sling 130 that are covered by the folds, wrinkles, creases, or the like. The optional plurality of fans 270 can be used to increase the effectiveness of the o-zone gas in permeating throughout the folds, wrinkles, creases, etc. of the laundry sling 130 by forcing produced o-zone gas surrounding the sanitizing lamp 230 into the laundry sling 130. Not only can the optional plurality of fans 270 force o-zone gas into the laundry sling 130, but the optional plurality of fans 270 force additional, new ambient air towards the sanitizing lamp 230, increasing the production of o-zone gas (e.g., by providing more $O_2$ molecules to be broken down by the sanitizing wavelength and more $O_2$ to combine with the resulting O molecules).

In addition to circulating o-zone gas within the laundry sling 130, the optional plurality of fans 270 can be used to cool the sanitizing lamp 230. Because the sanitizing system 200 may be used in laundry facilities with high temperatures and humidity levels, the plurality of fans 270 can also be used to cool the sanitizing lamp 230 and maintain an optimal operating temperature of the sanitizing lamp 230, which increases the power consumption efficiency of the sanitizing lamp 230, the effectiveness of the sanitizing lamp 230, and/or the useful life of sanitizing lamp 230.

According to some implementations of the present disclosure, the sanitizing system 200 can further include a generally cylindrical lamp cover (not shown) coupled to the bracket 210. More specifically, the generally cylindrical lamp cover (not shown) surrounds the sanitizing lamp 230, the socket 236, and the ballast 238 when the sanitizing lamp 230 is in the retracted position (FIGS. 5B and 6A) and has a bottom opening. While the sanitizing lamp 230 has been described herein as providing the sanitizing wavelength of light in response to being in the extended position (e.g., FIGS. 5C and 6B), the sanitizing lamp 230 can also continuously emit the sanitizing wavelength of light. Thus, when the sanitizing lamp 230 continuously emits light, the generally cylindrical lamp cover can be used to prevent or substantially inhibit the sanitizing wavelength of light from escaping the lamp cover. When the sanitizing lamp 230 is in the extended position (e.g., as in FIGS. 5C and 6B), the distal end 234 of sanitizing lamp 230 extends past the bottom opening of the generally cylindrical lamp cover such that the sanitizing wavelength of light can be emitted on, for example, the laundry sling 130.

In some implementations, the sanitizing system 200 can further include a cover (not shown) coupled to the bracket 210 for covering the upper opening 136 of the laundry sling 130 when the bracket 210 is in the second position. The cover (not shown) is generally the same shape and/or size as the upper opening 136 of the laundry sling 130 (e.g., the support ring 132) such that the cover (not shown) can be used to cover at least a portion of the upper opening 136. The cover also includes a generally central aperture and/or a slot for permitting the sanitizing lamp 230 to extend therethrough. In this manner, the cover can be used to inhibit or prevent the escape of o-zone gas and/or the sanitizing wavelength of light produced by the sanitizing lamp 230 from the interior of the laundry sling 130 and increases the effectiveness of the sanitizing wavelength of light and/or o-zone gas in sterilizing the interior surface of the laundry sling 130. In other implementations, the interior surface of the laundry sling 130 can include a reflective coating to aid the sanitizing lamp 230 in substantially sanitizing the interior surface. The reflective coating multiplies the effectiveness of the sanitizing lamp 230 by continuously reflecting the sanitizing wavelength of light emitted by the sanitizing lamp 230 within the interior of the laundry sling 130.

According to some implementations of the present disclosure, a sanitizing system (not shown) that is similar to the sanitizing system 1 and the sanitizing system 200 described herein includes a bracket, a sanitizing lamp, and a lamp actuator. Like the sanitizing systems 1 and 200, the sanitizing system is used to sanitize a laundry sling suspended from one or more support rails of a laundry transport system. The sanitizing lamp and the lamp actuator are the same as, or similar to, the sanitizing lamp 230 and the lamp actuator 250 of the sanitizing system 200. The bracket is similar to the bracket 210 of the sanitizing system 200, but differs in that instead of being coupled to the one or more support rails of the laundry transport system, the bracket is coupled to a support structure suspended above the one or more support rails. And rather than being pivotable about a first and a second pivot point relative to the one or more support rails like the bracket 210, the bracket is fixed relative to the one or more support rails of the laundry transport system (e.g., the bracket is positioned in a similar orientation as the bracket 210 when in the second position shown in FIG. 5B).

In such implementations, the sanitizing lamp and the lamp actuator are coupled to the bracket such that the sanitizing lamp is positioned generally vertical (e.g., perpendicular relative to the one or more support rails in a similar orientation as the sanitizing lamp 230 shown in FIG. 5B). In this position, the laundry sling of the laundry transport system can move past the bracket and the sanitizing lamp without being inhibited by the various components of the sanitizing system. To position at least a portion of the sanitizing lamp within the laundry sling for sanitizing (e.g., similar to the distal end 234 of the sanitizing lamp 230 shown in FIGS. 6A and 6B), the lamp actuator moves the sanitizing lamp to an extended position in the same, or similar, manner as the lamp actuator 250 of the sanitizing system 200. In the extended position, the sanitizing lamp sanitizes an interior surface of the laundry sling in the same or similar manner as the sanitizing lamps 30 and 230 described herein. This sanitizing system can also include a lamp cover that is the same as, or similar to, the generally cylindrical lamp cover described above.

Referring generally to FIGS. 7A-9B, a sanitizing system 700 includes an outer housing 710, an inner track 720, a transport mechanism 730, a sanitizing lamp assembly 740, an actuator 750, a fan 760, and a controller 770. Like the sanitizing systems 1 and 200 described herein, the sanitizing system 700 is generally used to substantially sanitize one or more laundry slings suspended from one or more support rails. More specifically, the actuator 750 causes the transport mechanism 730 to move relative to the inner track 720 such that (i) at least a portion of the lamp assembly 740 is positioned within the laundry sling and (ii) the lamp assembly 740 provides a sanitizing wavelength of light to substantially sterilize an interior surface of a laundry sling.

Figure 7A:
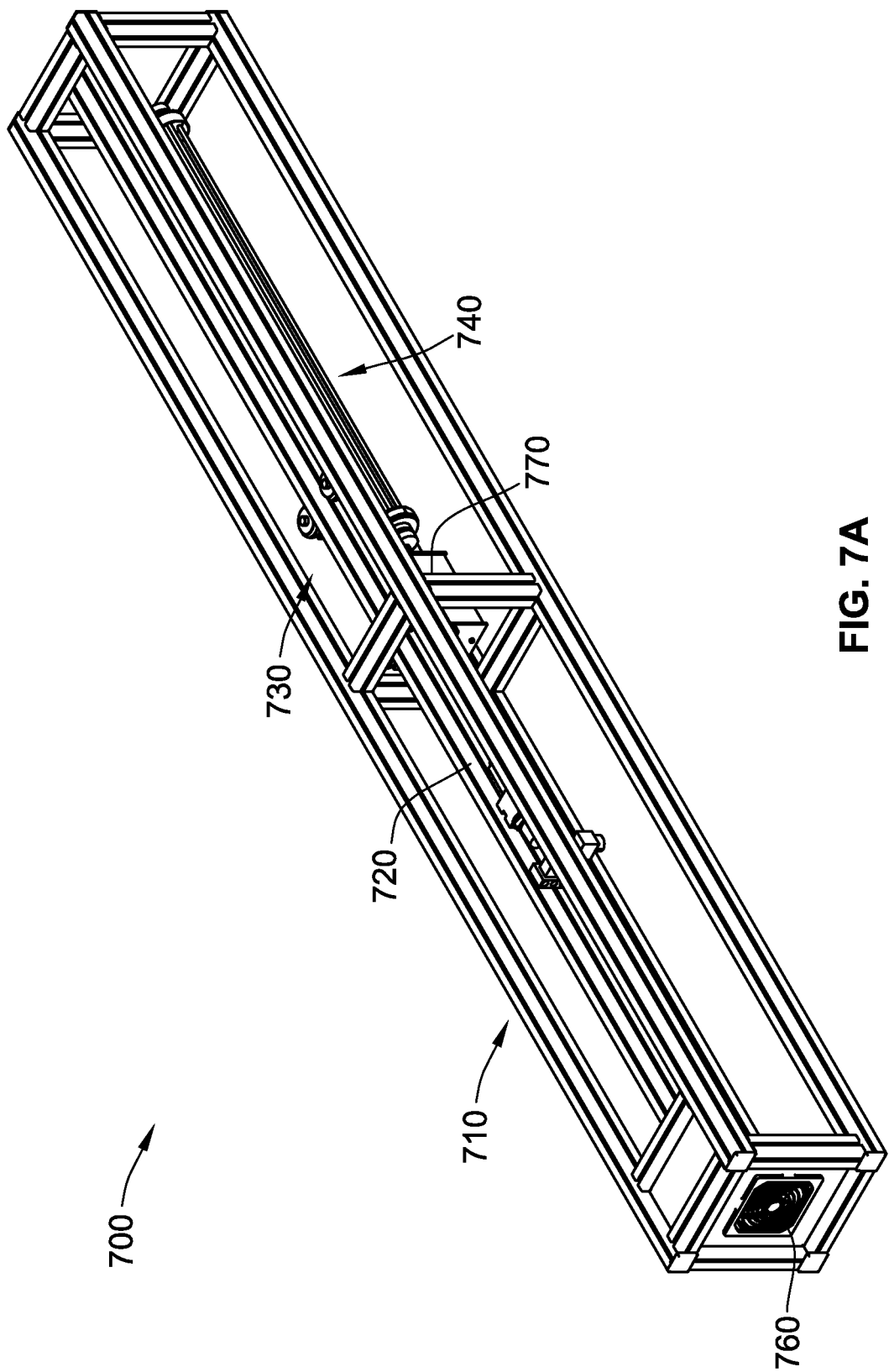
FIG. 7A is a perspective view of a sanitizing system according to some implementations of the present disclosure.
Figure 7B:
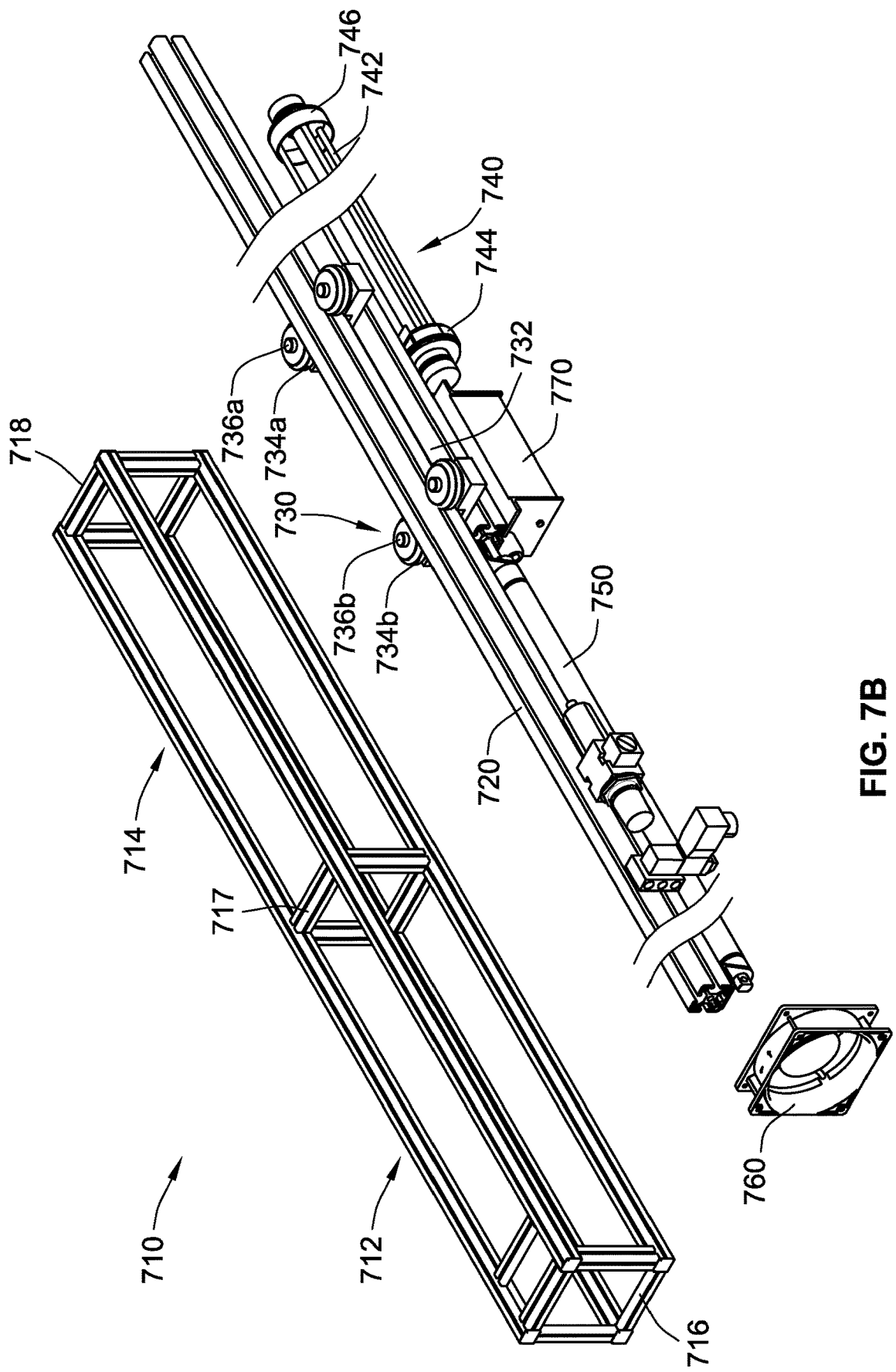
FIG. 7B is partially exploded view of the sanitizing system of FIG. 7A according to some implementations of the present disclosure.

As best shown in FIGS. 7A and 7B, the outer housing 710 is generally used to house and support the various elements of the sanitizing system 700 described herein and includes an upper portion 712 and a lower portion 714 (FIG. 7B). The upper portion 712 extends between an upper end 716 of the outer housing 710 and a middle portion 717. Similarly, the lower portion 714 extends between the middle portion 717 and a lower end 718. More specifically, as shown, each of the upper end 716, the middle portion 717, and the lower end 718 of the outer housing 710 includes four horizontal support elements. The upper portion 712 includes four vertical support elements that extend between the upper end 716 and the middle portion 717. Similarly, the lower portion 714 includes four vertical support elements that extend between the middle portion 717 and the lower end 718. The horizontal support elements and the vertical support elements of the outer housing 710 are shown as having a generally rectangular shape, although other shapes and sizes are possible (e.g., a generally cylindrical shape, a generally triangular shape, a generally polygonal shape, etc., or any combination thereof).

As shown, the outer housing 710 has a generally rectangular configuration, although other configurations are possible (e.g., a generally cylindrical configuration, a triangular configuration, a polygonal configuration, or any other suitable configuration or shape). The outer housing 710 can have an overall length (between the upper end 716 and the lower end 718) that is, for example, between about four feet and about twelve feet. Preferably, the overall length of the outer housing 710 is between about seven feet and about nine feet. More generally, the length of the outer housing can be selected such that the lamp assembly 740 and the actuator 750 can be stored therein (e.g., such that the actuator 750 can be disposed within the upper portion 712 and lamp assembly 740 can be disposed within the lower portion 714). Thus, while the upper portion 712 and the lower portion 714 are shown as having the same or similar lengths, the upper portion 712 and the lower portion 714 can have different lengths, for example, to allow the lamp assembly 740 and/or the actuator 750 to be stored therein, respectively. The width of the outer housing 710 can be, for example, between about five inches and about twenty inches. Preferably, the width of the outer housing 710 is between about nine inches and about twelve inches. More generally, the width of the outer housing 710 can be selected such that the components of the sanitizing system 700 described herein (e.g., the inner track 720, the transport mechanism 730, the lamp assembly 740, the actuator 750, the fan 760, and the controller 770) can be disposed within the outer housing 710. While the upper portion 712 and the lower portion 714 are shown as having the same or similar width, in some implementations, the upper portion 712 and the lower portion 714 can have different widths.

While the outer housing 710 is shown as being generally open (e.g., the internal components are generally exposed to the environment), the outer housing 710 can include an outer shell (not shown) that substantially covers the exterior of the outer housing 710, except for the lower end 718 to permit the lamp assembly 740 to extended from the outer housing 710 as described in further detail herein. The outer shell can be substantially the same shape as the outer housing 710 (e.g., generally rectangular), or a different shape than the outer housing 710 (e.g., generally cylindrical). The outer shell can also aid in directing air moved by the fan 760 through the lower end 718 of the outer housing 710.

Figure 7C:
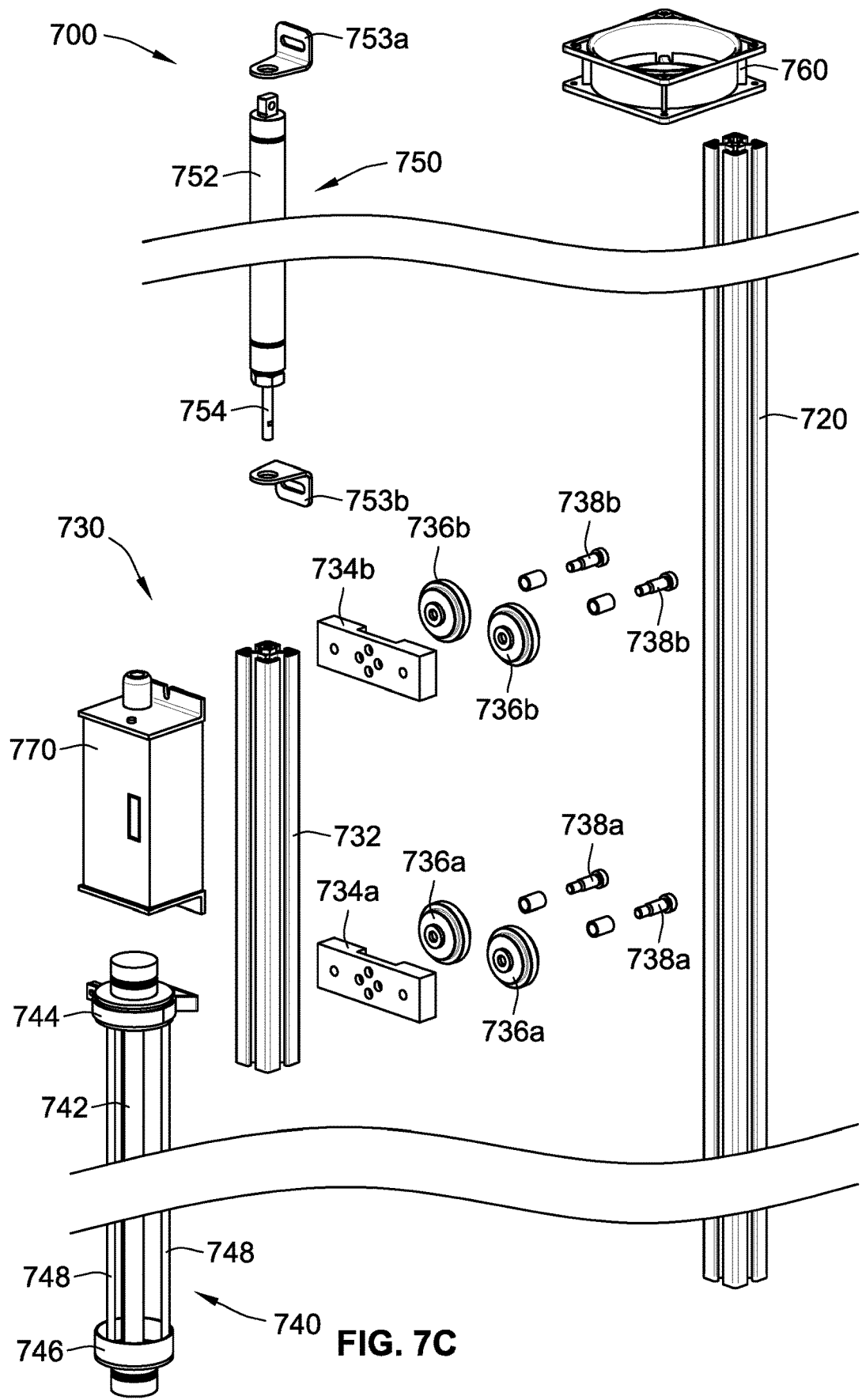
FIG. 7C is further exploded view of the sanitizing system of FIG. 7B according to some implementations of the present disclosure.
Figure 7D:
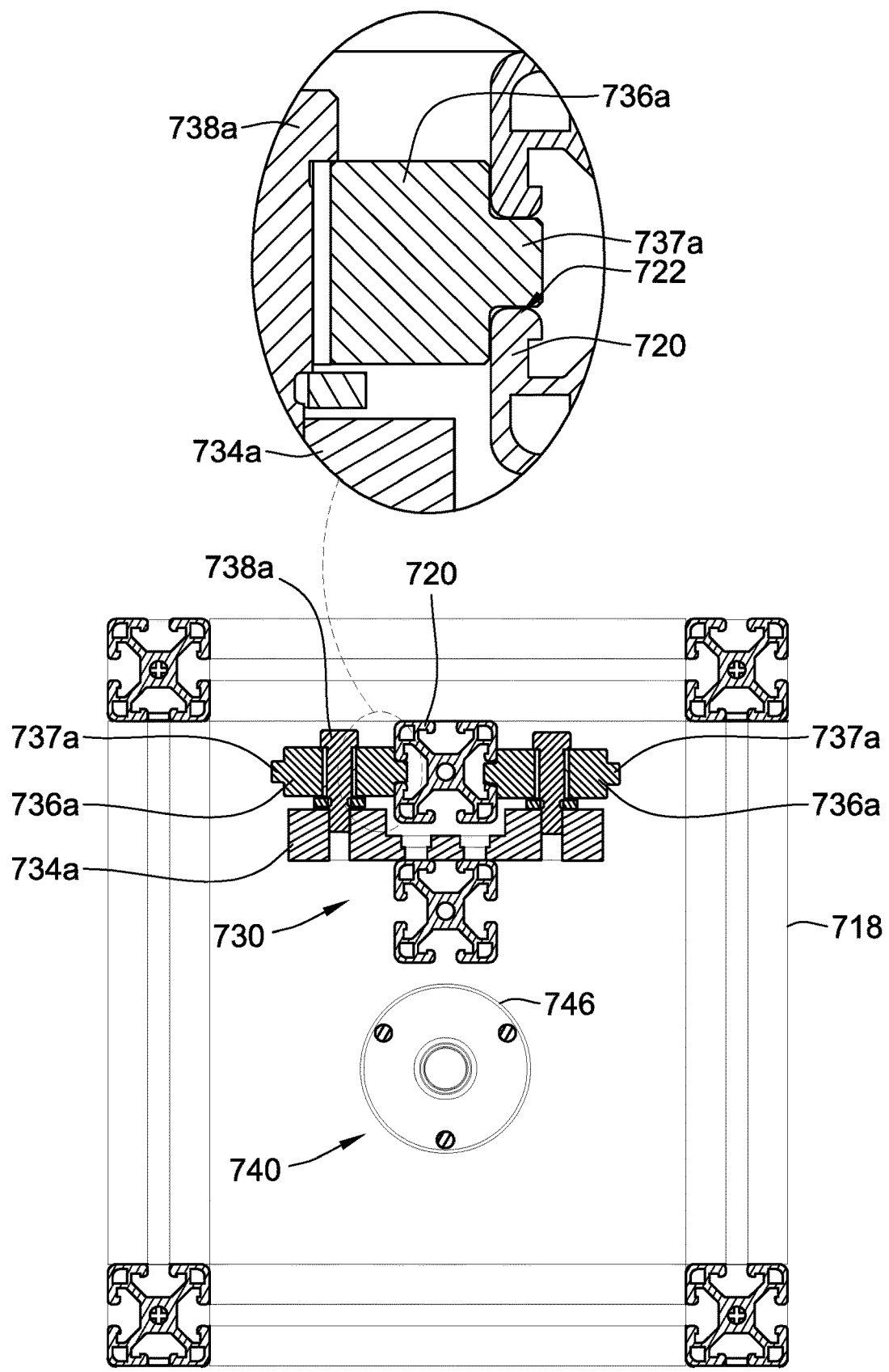
FIG. 7D is a bottom view of the sanitizing system of FIG. 7A according to some implementations of the present disclosure.

Referring generally to FIGS. 7C and 7D, the transport mechanism 730 includes a support member 732, a first support bracket 734a, a first pair of opposing wheels 736a, a first pair of axles 738a, a second support bracket 734b, a second pair of opposing wheels 736b, and a second pair of axles 738b. As best shown in FIG. 7D, the first support bracket 834a is coupled to the support member 732 (e.g., via a welded connection, one or more fasteners, etc.) The first pair of opposing wheels 736a is coupled to the first support bracket 734a via the first pair of axles 738a, which facilitate rotation of the first pair of opposing wheels 736a relative to the first support bracket 734a. As best shown in FIG. 7D, each of the first pair of opposing wheels 736a includes a tongue 737a protruding from an outer surface thereof. The second pair of opposing wheels 736b each include a tongue is the same as the tongue 737a of each of the first pair of opposing wheels 736a shown in FIG. 7D. Each tongue 737a is sized and shaped to engage a groove 722 of the inner track 720 to aid in coupling the transport mechanism 730 to the inner track 720 and allowing the transport mechanism 730 to be moveable with respect to the inner track 720.

Referring to FIG. 7C, the lamp assembly 740 includes a sanitizing lamp 742, an upper end 744, a lower end 746, and a plurality of support bars 748. The sanitizing lamp 742 is the same as, or similar to, the sanitizing lamp 30 (FIG. 1) and the sanitizing lamp 230 (FIGS. 4A-6B) described herein and is configured to emit a sanitizing wavelength of light (e.g., a wavelength between about 180 nm and about 260 nm). The sanitizing lamp 742 is disposed between an upper end 744 of the lamp assembly 740 and the lower end 746 of the lamp assembly 740. The plurality of support bars 748 extend between the upper end 744 and the lower end 746 of the lamp assembly 740 and aid in protecting the sanitizing lamp 742 from damage (e.g., breaking). For example, if the lamp assembly 740 is extended into the laundry sling and the laundry sling is unintentionally moved and contacts the lamp assembly 740, the plurality of support bars 748 aid in preventing this unintentional contact from breaking the sanitizing lamp 742. As shown, the plurality of support bars 748 include three support bars, however, any suitable number of support bars can be used (e.g., two support bars, four support bars, eight support bars, etc.)

While the lamp assembly 740 is shown as including one sanitizing lamp 742, in some implementations, the lamp assembly 740 can include a plurality of sanitizing lamps that are the same as, or similar to, the sanitizing lamp 742 (e.g., two sanitizing lamps, three sanitizing lamps, five sanitizing lamps, etc.) For example, the lamp assembly 740 can include a first sanitizing lamp configured to emit a first sanitizing wavelength of light (e.g., about 254 nm) and a second sanitizing lamp configured to emit a second sanitizing wavelength of light that is different than the first sanitizing wavelength of light (e.g., about 185 nm). In such implementations, the first sanitizing lamp and the second sanitizing lamp can be configured to emit the first and second sanitizing wavelengths of light simultaneously or successively.

The actuator 750 is similar to the bracket actuator 40 and the lamp actuator 50 (FIG. 1) described herein. As best shown in FIGS. 8B and 8C, the actuator 750 includes a piston cylinder 752 and a piston 754 that is disposed within, and moveable relative to, the piston cylinder 752 between a retracted position and an extended position. A spring (not shown) disposed in the piston cylinder 752 to generally bias or urge the piston 754 to remain in the retracted position. The actuator 750 is coupled to a fluid reservoir (not shown) that is the same as, or similar to, the fluid reservoir 4 (FIG. 1) described herein via, for example, a connection tube. When fluid from the fluid reservoir (e.g., compressed air) is forced into the piston cylinder 752 (e.g., through a valve), the fluid overcomes the spring bias and causes the piston 754 to move relative to the piston cylinder 754 from the retracted position to the extended position. In this manner, the piston 754 can be moved between a retracted position and an extended position.

Figure 8A:
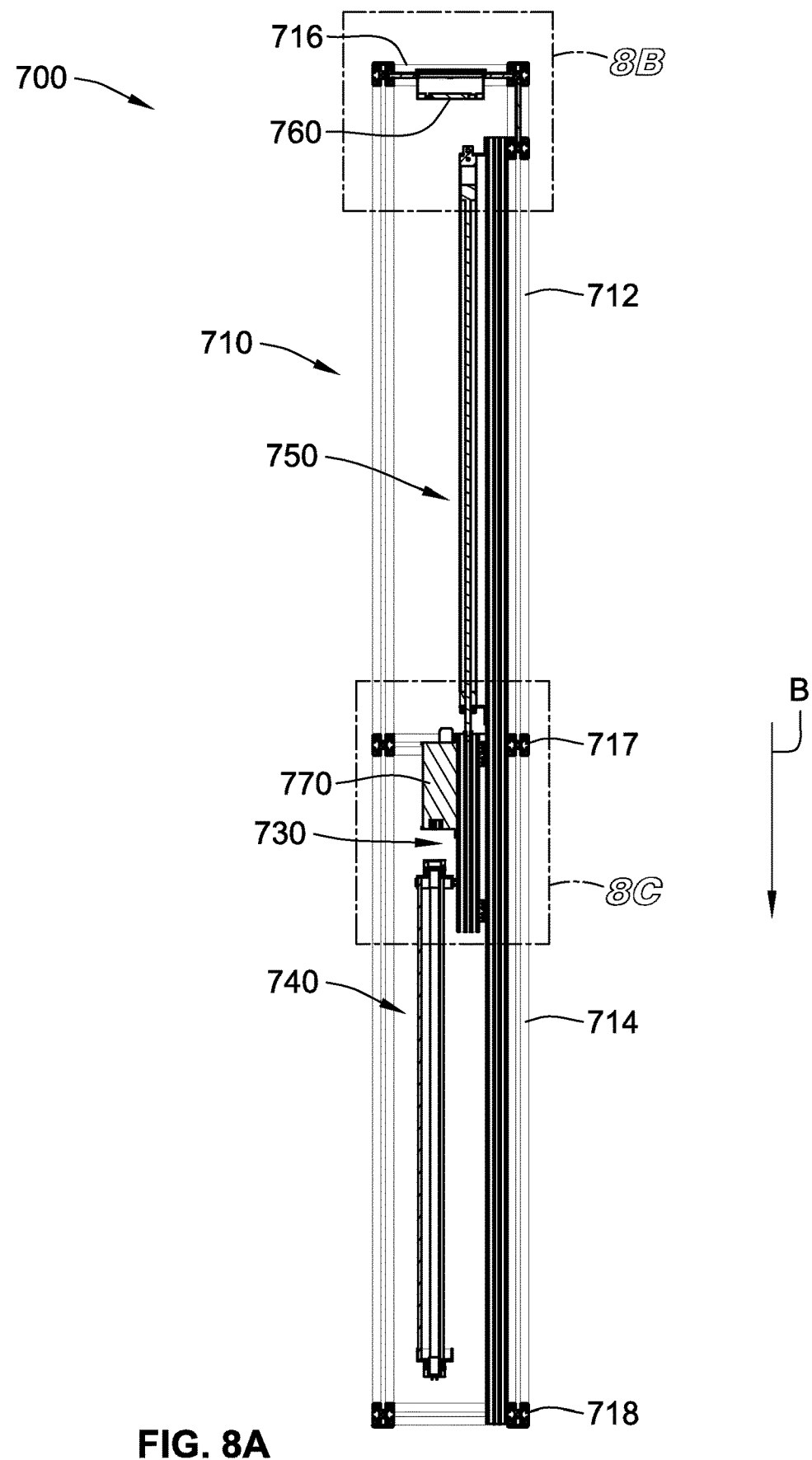
FIG. 8A is a side view of the sanitizing system of FIG. 7A according to some implementations of the present disclosure.
Figure 8B:
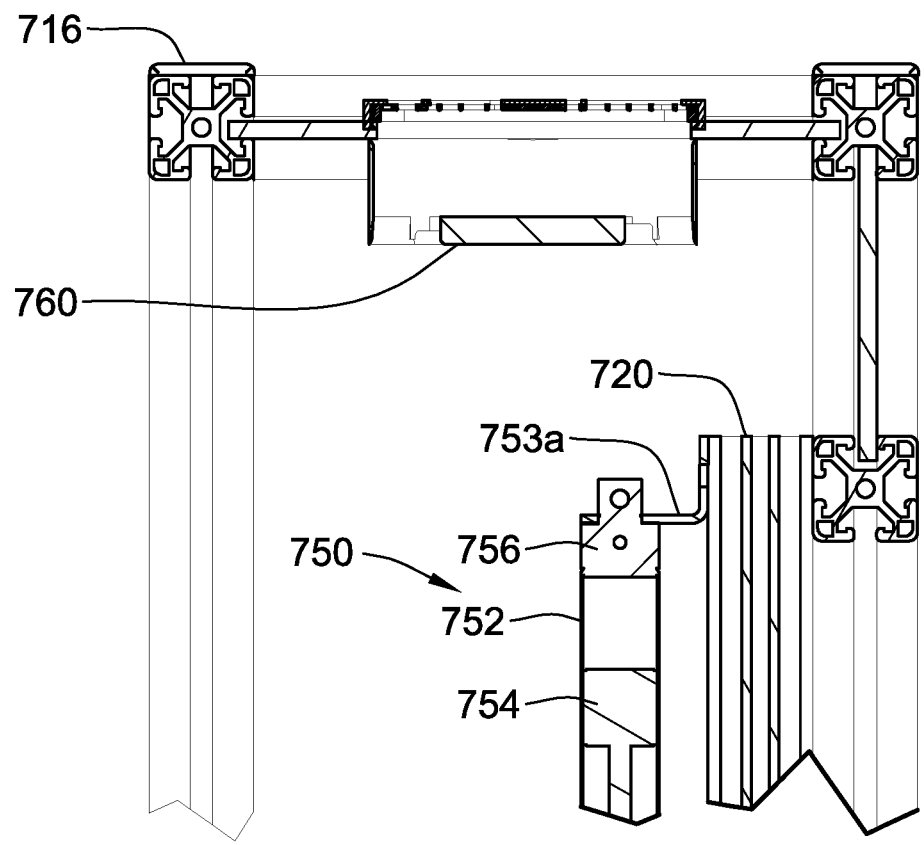
FIG. 8B is an enlarged partial side view of the sanitizing system of FIG. 8A according to some implementations of the present disclosure.
Figure 8C:
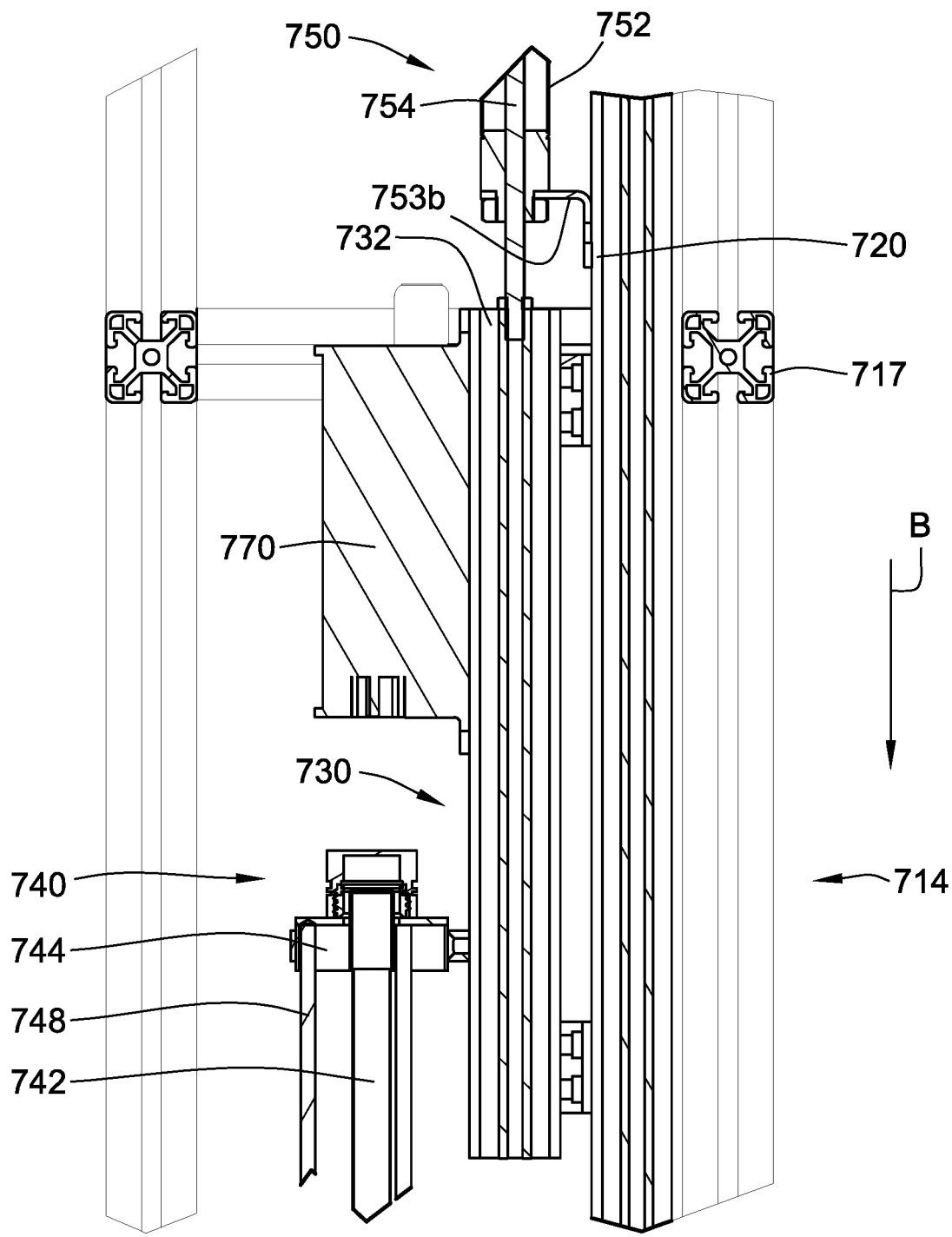
FIG. 8C is another enlarged partial side view of the sanitizing system of FIG. 8A according to some implementations of the present disclosure.

Referring generally to FIGS. 8A-8C, the actuator 750 is disposed within the upper portion 712 of the outer housing 710 and is coupled to the inner track 720. As best shown in FIG. 8B, an upper end 756 of the piston cylinder 752 of the actuator 750 is coupled to the inner track 720 such that the upper end 756 is within the upper portion 712 of the outer housing 710 and generally adjacent to the upper end 716 of the outer housing 710. The upper end 756 of the actuator 750 can be directly or indirectly coupled to the inner track 720 using, for example, a first bracket 753a. As best shown in FIG. 8B, a lower end 758 of the piston cylinder 752 of the actuator 750 is coupled to the inner track 720 such that the lower end 758 is within the upper portion 712 of the outer housing 710 and is generally adjacent to the middle portion 717 of the outer housing 710. Like the upper end 756, the lower end 758 can be directly or indirectly coupled to the inner track 720 using, for example, a second bracket 753b.

The transport mechanism 730 is coupled to both the actuator 750 and the inner track 720. More specifically, as best shown in FIG. 8C, the piston 754 of the actuator 750 is coupled to the support member 732 of the transport mechanism 730. The piston 754 can be coupled directly or indirectly to the support member 732 using, for example, a welded connection, an adhesive connection, a press fit or interference fit connection, a snap fit connection, a collar, or the like, or any combination thereof. As described herein and best shown in FIG. 7D, the transport mechanism 730 is coupled to the inner track 720 via the first pair of opposing wheels 736a and the second pair of opposing wheels 736b such that the transport mechanism 730 is moveable along the inner track 720. Thus, movement of the actuator 750 (e.g., moving the piston 754 between the retracted position and the extended position) causes corresponding movement of the transport mechanism 730 along the inner track 720.

As best shown in FIG. 8C, the lamp assembly 740 is coupled to the transport mechanism 730. More specifically, upper end 744 of the lamp assembly 740 is coupled, directly or indirectly, to the support member 732 of the transport mechanism 730 (e.g., via a welded connection, an adhesive connection, a bracket, a collar, or the like, or any combination thereof). Thus, movement of the transport mechanism 730 (e.g., movement caused by corresponding movement of the actuator 750) causes corresponding movement of the lamp assembly 740 and the sanitizing lamp 742 contained therein relative to the inner track 720.

The controller 770 is the same as, or similar to, the controller 3 (FIG. 1) described herein and is generally used to control the operation of the various components of the sanitizing system 700. The controller 770 is communicatively coupled to one or more of the actuator 750 the sanitizing lamp 742 of the lamp assembly 740, and the fan 760. The controller 770 can include one or more processors, one or more memory devices, and/or one or more communication modules. As shown, the controller 770 is coupled to the support member 732 of the transport mechanism 730, although more generally the controller 770 can be positioned anywhere within or on the outer housing 710. Alternatively, the controller 770 may be decentralized and physically separated from the outer housing 710 and the other components of the sanitizing system 700 (e.g., the controller 770 is wirelessly connected to the various components of the sanitizing system 700).

Figure 9A:
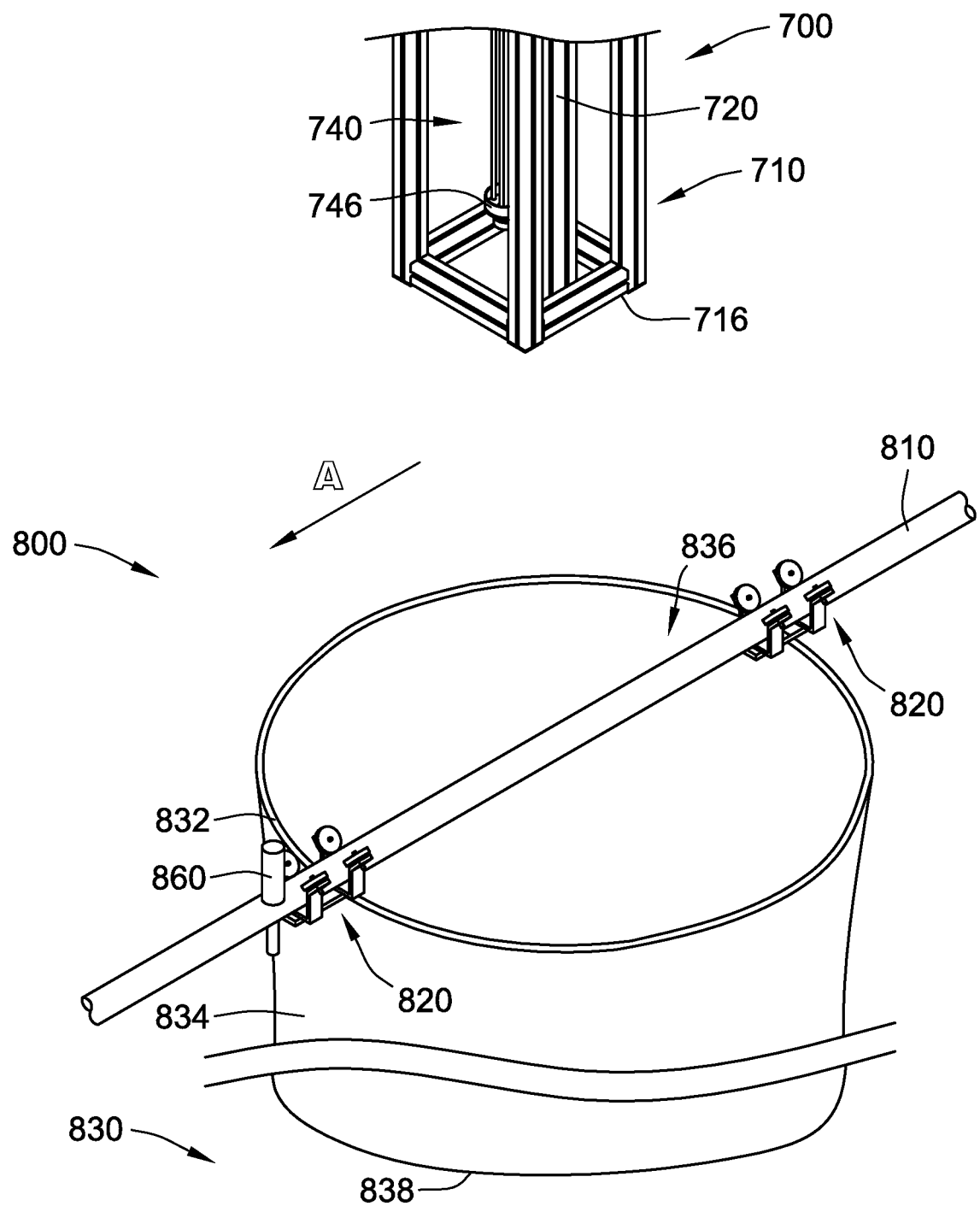
FIG. 9A is a perspective view of the sanitizing system of FIG. 7A suspended above a laundry transport system with a sanitizing lamp of the sanitizing system in a retracted position according to some implementations of the present disclosure.
Figure 9B:
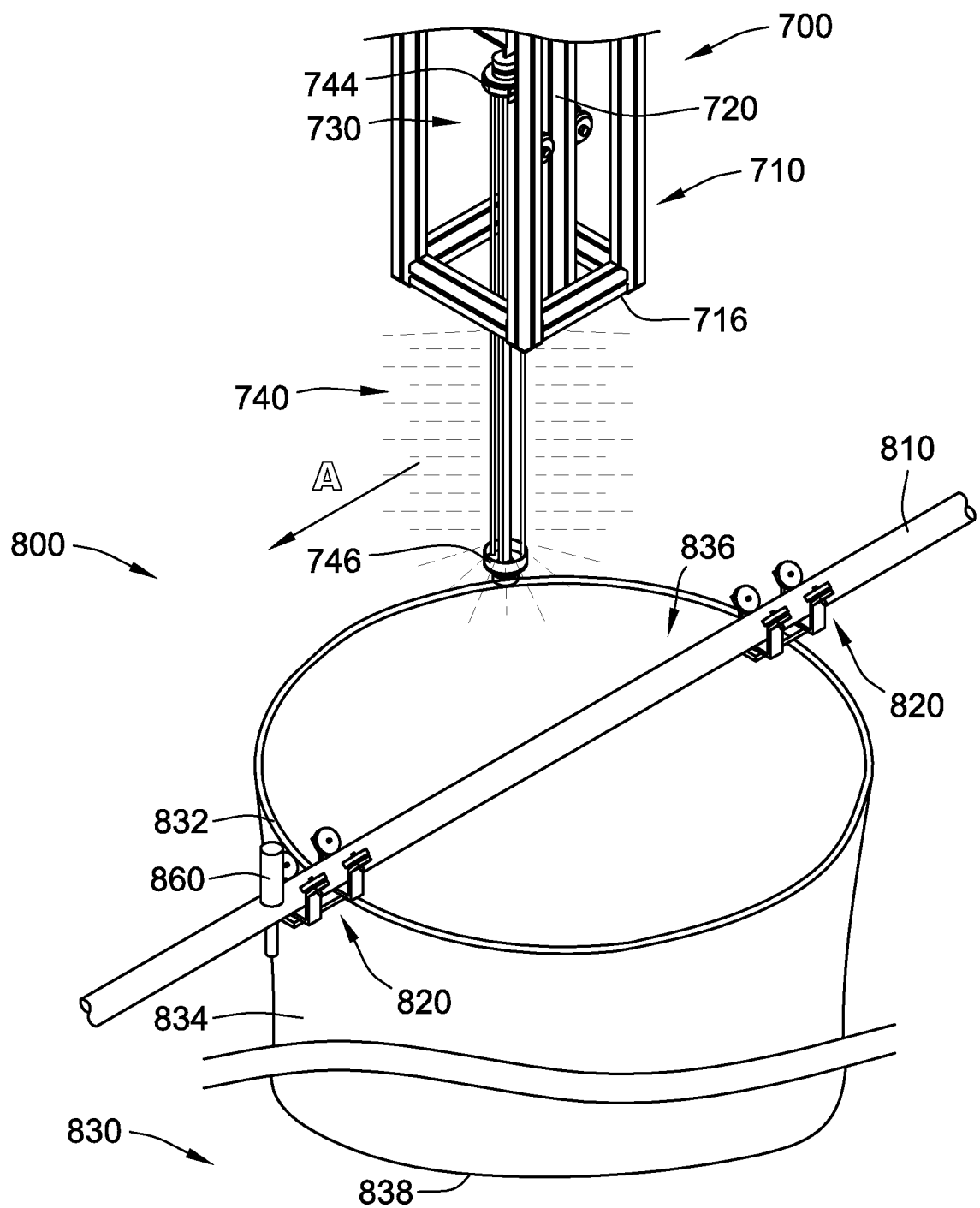
FIG. 9B is a perspective view of the sanitizing system and laundry transport system of FIG. 9A with the sanitizing lamp in an extended position according to some implementations of the present disclosure.

Referring to FIGS. 9A and 9B, in some implementations, the sanitizing system 700 is used to substantially sanitize a laundry sling 830 of a laundry transport system 800. The laundry transport system 800 is similar to the laundry transport system 100 described herein (FIG. 2) in that the laundry transport system 800 includes a plurality of trolleys 820 and a laundry sling 830. The laundry transport system 800 differs from the laundry transport system 100 in that the laundry transport system 800 includes a single support rail 810, as opposed to two support rails 110a and 110b. The sanitizing system 700 is suspended above the support rail 810, for example, by coupling the upper end 716 of the outer housing 710 to a ceiling of a structure and/or another support structure which is itself coupled to or suspended from a ceiling of a structure (e.g., an I-beam, another support rail, or the like). As shown, the outer housing 710 is suspended such that the outer housing 710 is generally perpendicular to the support rail 810 and the lower end 718 is generally adjacent to the support rail 810.

To extend at least a portion of the lamp assembly 740 and the sanitizing lamp 742 into the laundry sling 830 during use, the outer housing 710 is suspended above the laundry transport system 800 such that a central axis of the lamp assembly 740 is offset from the support rail 810. This offset prevents the lamp assembly 740 from contacting the top of the support rail 810 when moved to the extended position (FIG. 9B). For example, the central axis of the lamp assembly 740 can be offset by between about one inch and about twenty-four inches from the support rail 810, between about three inches and about twelve inches from the support rail 810, between about four inches and about eight inches from the support rail 810, or by any other suitable distance to aid in preventing contact between the support rail 810 and the lamp assembly 740.

The laundry transport system 800 also optionally includes a stopper 860 that is the same as, or similar to, the stopper 60 and the stopper 160 described herein and a sensor (not shown) that is the same as, or similar to, the sensor 168 (FIGS. 3A and 3B) described herein. The stopper 860 and the sensor are communicatively coupled (e.g., using a wired or wireless connection) to the controller 770 of the sanitizing system 700. Like the stopper 60 and the stopper 160 described herein, the stopper 860 is used to inhibit movement of the laundry sling 830 along the support rail 810.

To substantially sanitize an interior surface of the laundry sling 830, the controller 770 first determines, via the sensor, that the laundry sling 830 is generally adjacent to the lower end 718 of the outer housing 710 of the sanitizing system 700. Responsive to this determination, the controller 770 actuates the stopper 860 to inhibit further movement of the laundry sling 830 such that the laundry sling 830 is positioned below the sanitizing system 700 (e.g., as shown in FIGS. 9A and 9B). The controller 770 then actuates the actuator 750 such that the piston 754 moves from the retracted position to the extended position, causing corresponding movement of the transport mechanism 730 and the lamp assembly 740. This causes the lamp assembly 740 to move from a retracted position (FIG. 9A) to an extended position (FIG. 9B) where at least a portion of the sanitizing lamp 742 is positioned within the laundry sling 830.

Like the laundry sling 130, the laundry sling 830 includes a support ring 832, a body portion 834, and a closed bottom 838. When the lamp assembly 740 is in the extended position (FIG. 9B), the lower end 746 of the lamp assembly 740 is positioned within the body portion 834 of the laundry sling 830 at a predetermined distance from the closed bottom 838. The predetermined distance can be, for example, at least about 80% of a distance between the upper opening 836 and the closed bottom 838 of the laundry sling 830, at least about 60% of a distance between the upper opening 836 and the closed bottom 838 of the laundry sling 830, at least about at least about 40% of a distance between the upper opening 836 and the closed bottom 838 of the laundry sling 830, at least about 20% of a distance between the upper opening 836 and the closed bottom 838 of the laundry sling 830, at least about 10% of a distance between the upper opening 836 and the closed bottom 838 of the laundry sling 830, etc. The effectiveness of the sanitizing wavelength of light emitted by the sanitizing lamp 742 in sanitizing the laundry sling 830 is generally a function of the predetermined distance. In other words, the lower end 746 of the lamp assembly 740 must extend far enough into the upper opening 836 of the laundry sling 830 for the sanitizing wavelength of light to be most effective in sanitizing the entire interior surface of the laundry sling 830.

The controller 770 also actuates the sanitizing lamp 742 to cause the sanitizing lamp 742 to emit a sanitizing wavelength of light to aid in substantially sanitizing an interior surface of the laundry sling 830. The controller 770 actuates the sanitizing lamp 742 responsive to the beginning of movement between the first position and the second position, or responsive to at least a portion of the sanitizing lamp 742 being positioned in the laundry sling 830. In some implementations, the controller 770 causes the sanitizing lamp 742 to emit a plurality of sequential wavelengths of sanitizing light (e.g., a UV-producing wavelength of light then an o-zone gas producing wavelength of light). As described herein, in some implementations, the sanitizing lamp 742 emits a sanitizing wavelength of light that is between about 180 nm and about 190 nm to produce a volume of o-zone gas. In such implementations, the controller 770 actuates the fan 760 to cause the fan 760 to move air adjacent to the sanitizing lamp 742 to cause the air and the volume of produced o-zone gas to exit the outer housing 710 and/or mix within the laundry sling 830 to aid in substantially sanitizing the interior surface of the laundry sling 830.

After a predetermined sanitizing period (e.g., between about one second and about one minute, between about five seconds and ten seconds, between about five seconds and about twenty seconds, between about five seconds and fifty seconds, and/or between about five seconds and 110 seconds), the controller 770 actuates the actuator 750 to move the piston 754 from the extended position to the retracted position, causing corresponding movement of the transport mechanism 730 and the lamp assembly 740. This causes the lamp assembly 740 to move from the second, extended position (FIG. 9B) to the first, retracted position (FIG. 9A). The controller 770 then actuates the stopper 860 to resume movement of the laundry sling 830 along the support rail 810.

While the sanitizing system 700 is shown and described herein as being used with the laundry transport system 800 (FIGS. 9A and 9B) to sanitize the laundry sling 830 suspended from one support rail 810, in other implementations, the sanitizing system 700 can also be used with the laundry transport system 100 to sanitize the laundry sling 130 suspended from two support rails 110a and 110b (FIG. 2). In other words, the sanitizing system 700 can be used to sanitize one or more laundry slings that are suspended from any number of support rails (e.g., one rail, two rails, three rails, four rails, etc.)

Figure 10A:
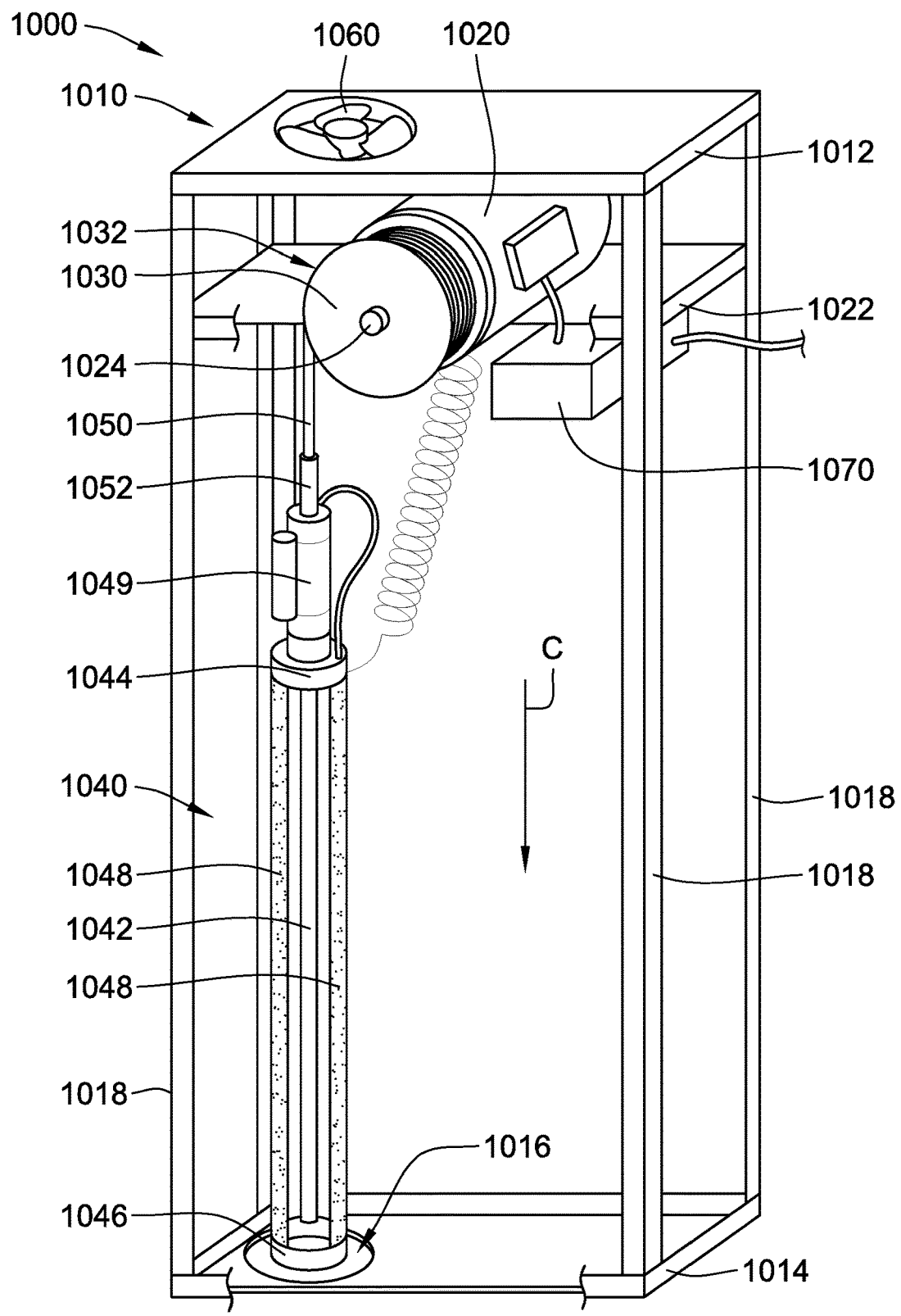
FIG. 10A is a perspective view of a sanitizing system with a sanitizing lamp in a retracted position according to some implementations of the present disclosure.
Figure 10B:
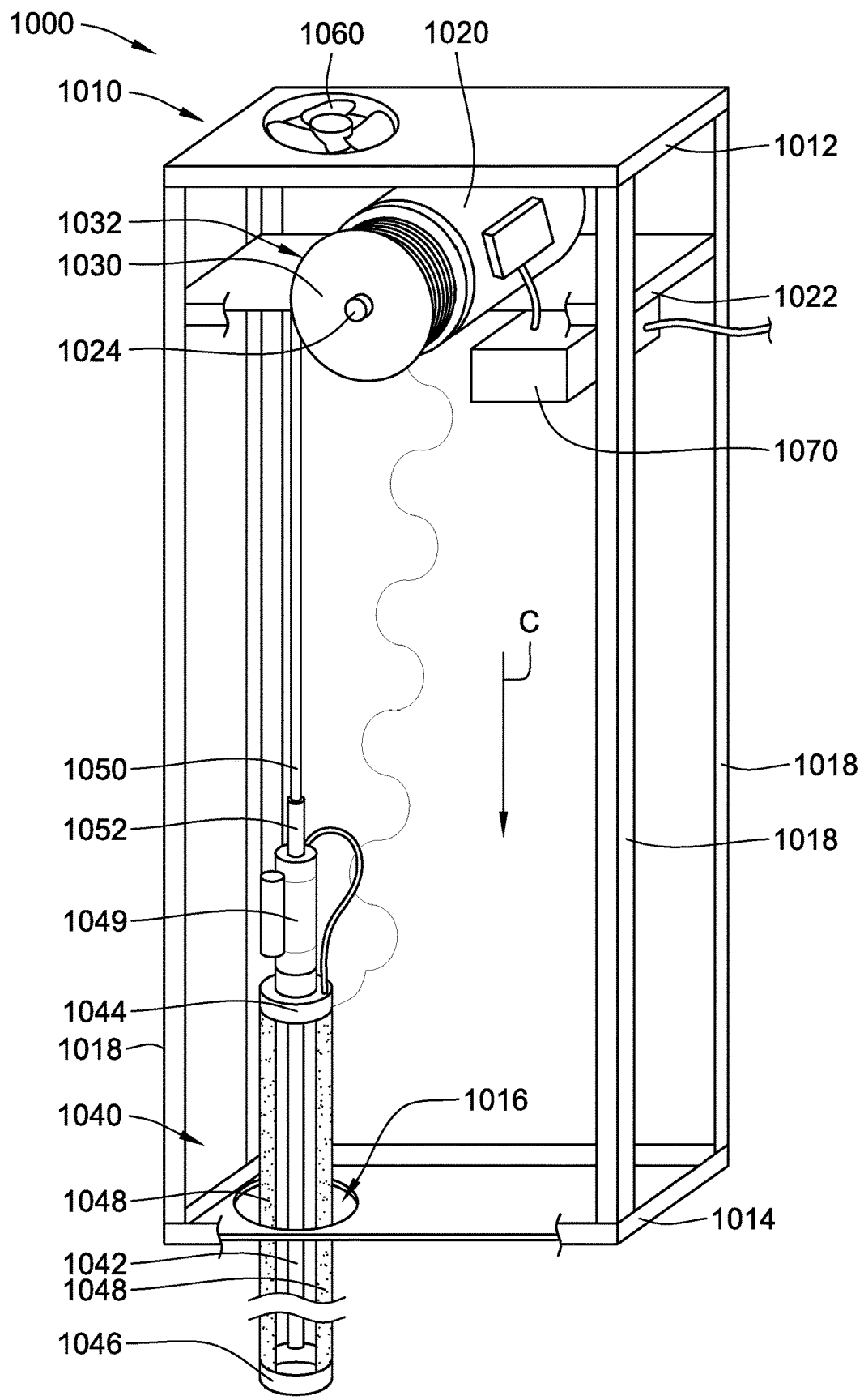
FIG. 10B is a perspective view of the sanitizing system of FIG. 10A with the sanitizing lamp moved to an extended position according to some implementations of the present disclosure.

Referring generally to FIGS. 10A and 10B, a sanitizing system 1000 includes a housing 1010, a motor 1020, a winding device 1030, a lamp assembly 1040, a cable 1050, a fan 1060, and a controller 1070. The sanitizing system 1000 is similar to the sanitizing systems 1, 200, 700 in that the sanitizing system 1000 is generally used for sanitizing a laundry sling (e.g., the laundry sling 830 of the laundry transport system 800 or laundry sling 130 of the laundry transport system 100).

The housing 1010 includes an upper end 1012, a lower end 1014, and a plurality of vertical support elements 1018. As shown, the various elements of the sanitizing system 1000 are disposed within and/or supported by the housing 1010. The plurality of vertical support elements 1018 includes four vertical support elements that extend between the upper end 1012 and the lower end 1014, although other numbers of vertical support elements are possible (e.g., two, five, six, ten, etc.) The lower end 1014 includes a lower opening 1016 that is sized and shaped to permit at least a portion of the lamp assembly 1040 to protrude from the housing 1010 during operation as described in further detail herein.

As shown, the housing 1010 has a generally rectangular configuration, although other shapes and configurations are possible (e.g., a cylindrical configuration, a triangular configuration, a polygonal configuration, etc.) The upper end 1012, the lower end 1014, and the plurality of vertical support elements 1018, or any combination thereof, can be separate and distinct components that are coupled to one another (e.g., using a welded connection, an adhesive connection, one or more fasteners, a press or interference fit, a snap fit, or the like, or any combination thereof). Alternatively, the upper end 1012, the lower end 1014, and the plurality of vertical support elements 1018, or any combination thereof can be unitary and/or monolithic. Further, while the housing 1010 is shown as being open for illustrative purposes, the housing 1010 can include an outer shell coupled to the plurality of vertical support elements 1018

The motor 1020 is coupled to the housing 1010 via a motor support bracket 1022. The motor support bracket 1022 can be coupled to the housing 1010 using a variety of mechanisms, such as, for example, a welded connection, an adhesive connection, one or more fasteners (e.g., a nut and bolt connection), a collar, or any combination thereof. Alternatively, the motor support bracket 1022 and at least a portion of the housing 1010 can be unitary and/or monolithic.

The motor 1020 is operatively coupled to the cable 1050, which is in turn coupled to the lamp assembly 1040, such that operation of the motor 1020 causes the lamp assembly 1040 to move between a retracted position (FIG. 10A) and an extended position (FIG. 10B). More specifically, a first end 1052 of the cable 1050 is coupled to the lamp assembly 1040 and a second end of the cable 1050 is coupled to the winding device 1030. The winding device 1030 is configured to aid in winding and unwinding at least a portion of the cable 1050. As shown, the winding device 1030 is a cylindrical spool with a flange 1032 that aids in winding at least a portion of the cable 1050 onto the winding device 1030. Alternatively, in some implementations, the winding device 1030 can include one or more pulleys, one or more spools, one or more bearings, or any combination thereof.

The motor 1020 is configured to rotate the winding device 1030 to cause at least a portion of the cable 1050 to be wound onto the winding device 1030, which causes a corresponding linear movement of the lamp assembly 1040. The motor 1020 includes a spindle 1024 that is coupled to the winding device 1030, either directly or indirectly (e.g., using one or more gears, belts, transmissions, or any combination thereof). The motor 1020 can be an electric stepper motor that is configured to rotate at a predetermined step rate (e.g., 200 steps per second at 200 steps per revolution provides 60 revolutions per minute). More generally, the motor 1020 can be an electric motor, such as a brushless direct current ("DC") electric motor or a brushed DC electric motor, a gas motor, such as an internal combustion motor, or any other suitable mechanism for rotating the winding device 1030.

The lamp assembly 1040 is the same as, or similar to, the lamp assembly 740 of the sanitizing system 700 described herein and includes a sanitizing lamp 1042, an upper end 1044, a lower end 1046, a plurality of support bars 1048, and a ballast 1049. The sanitizing lamp 1042 is configured to emit a sanitizing wavelength of light (e.g., between about 180 nm and about 260 nm). The sanitizing lamp 1042 is disposed between the upper end 1044 and the lower end 1046 of the lamp assembly 1040. The plurality of support bars 1048 extend between the upper end 1044 and the lower end 1046 of the lamp assembly 1040 and aid in protecting the sanitizing lamp 842 from damage (e.g., breaking). As shown, the plurality of support bars 1048 include three support bars, however, any suitable number of support bars can be used (e.g., two support bars, four support bars, eight support bars, etc.)

While the lamp assembly 1040 is shown as including one sanitizing lamp 742, in some implementations, the lamp assembly 1040 can include a plurality of sanitizing lamps that are the same as, or similar to, the sanitizing lamp 742 (e.g., two sanitizing lamps, three sanitizing lamps, five sanitizing lamps, etc.) For example, the lamp assembly 1040 can include a first sanitizing lamp configured to emit a first sanitizing wavelength of light (e.g., about 254 nm) and a second sanitizing lamp configured to emit a second sanitizing wavelength of light that is different than the first sanitizing wavelength of light (e.g., about 185 nm). In such implementations, the first sanitizing lamp and the second sanitizing lamp can be configured to emit the first and second sanitizing wavelengths of light simultaneously or successively.

As described herein, the cable 1050 has a first end 1052 that is coupled to the lamp assembly 1040 and a second end that is coupled to the winding device 1030 such that movement of the cable 1050 causes corresponding movement of the lamp assembly 1040. As shown, the first end 1052 of the cable 1050 is coupled to the ballast 1049 of the lamp assembly 1040. The first end 1052 of the cable 1050 can be terminated in various ways to couple the cable 1050 to the lamp assembly 1040 (e.g., the first end 1052 can be terminated with a loop using a clamp/clip, the first end 1052 can be welded or adhered to the lamp assembly 1040, the first end 1052 can be coupled to the lamp assembly 1040 using a collar, or any combination thereof). Alternatively, the first end 1052 of the cable 1050 can be coupled to other parts of the lamp assembly 1040, such as, for example, directly to the upper end 1044 of the lamp assembly 1040.

The cable 1050 can have any suitable size (e.g., diameter, length, etc.) and can be made from any suitable material (e.g., stainless steel, iron, copper, polymers, fibers, or any combination thereof) with a sufficient tensile strength to support the weight of the lamp assembly 1040. For example, the cable 1050 can have a diameter that is between about 0.05 inches and about 0.75 inches, between about 0.1 inches and about 0.5 inches, etc. Preferably, the cable 1050 is a stainless steel cable with a diameter that is between about 0.1 inches and about 0.3 inches.

The fan 1060 is the same as, or similar to, the fan 760 of the sanitizing system 700 described herein and is coupled to the upper end 1012 of the housing 1010. In some implementations, the sanitizing lamp 1042 of the lamp assembly 1040 is configured to emit a sanitizing wavelength of light that is between about 180 nm and about 190 nm to produce a volume of o-zone gas that aids in sanitizing an interior of a laundry sling. The airflow caused by the fan 1060 is generally directed downwards towards the lower opening 1016 of the lower end 1014 of the housing 1010 to aid in forcing produced o-zone gas out of the housing 1010 through the lower opening 1016 and to aid in mixing the o-zone gas within the interior of the laundry sling to substantially sterilizing the interior surface of the laundry sling. While the sanitizing system 1000 is shown as including one fan 1060, in some implementations, the sanitizing system 1000 can include a plurality of fans that are the same as, or similar to, the fan 1060 that are coupled to the same or different locations on or within the housing 1010 to aid in mixing the produced o-zone gas within the laundry sling. For example, the fan 1060 can be coupled to the upper end 1012 within the housing 1010 and a second fan can be coupled to the exterior surface of the lower end 1014 of the housing 1010).

The controller 1070 is coupled to the housing 1010 via the motor support bracket 1022 and is communicatively coupled to one or more of the motor 1020, the lamp assembly 1040, and the fan 1060. The controller 1070 is also electrically coupled to an external power supply (not shown) to provide power to the various components of the sanitizing system 1000. The controller 1070 generally includes one or more processors for executing instructions stored in one or more memory devices to control the operation of the components of the system 1000.

The controller 1070 can also be communicatively coupled to a sensor and a stopper (e.g., such as those described herein) to fully automate the sanitizing system 1000. For example, responsive to determining, using the sensor, that the laundry sling is positioned below the housing, the controller 1070 actuates the stopper to inhibit further movement of the laundry sling.

With movement of the laundry sling inhibited by the stopper, the controller 1070 is drives a motor control circuit that causes the motor 1020 to rotate and cause a corresponding rotation of the winding device 1030 and corresponding linear movement of the lamp assembly 1040. To move the lamp assembly 1040 from the retracted position (FIG. 10A) to the extended position (FIG. 10B) and into at least a portion of the laundry sling, the motor 1020 rotates in a first direction (e.g., clockwise or counterclockwise), causing rotation of the winding device 1030. As the winding device 1030 rotates, the cable 1050 beings to unwind from the winding device 1030, causing the lamp assembly to move in the direction of arrow C. Because the first end 1052 is coupled to the lamp assembly 1040, gravity aids in unwinding the cable 1050. As the lamp assembly 1040 moves in the direction of arrow C, at least a portion of the lamp assembly 1040 protrudes through the housing 1010 through the lower opening 1016 in the lower end 1014.

The motor 1020 continues to rotate the winding device 1030 for a predetermined time or a predetermined number of rotations until the lower end 1046 of the lamp assembly 1040 is positioned at a predetermined distance from the closed bottom of the laundry sling. The predetermined distance can be, for example, at least about 80% of a distance between the upper opening and the closed bottom of the laundry sling, at least about 60% of a distance between the upper opening and the closed bottom of the laundry sling, at least about 40% of a distance between the upper opening and the closed bottom of the laundry sling, at least about 20% of a distance between the upper opening and the closed bottom of the laundry sling, etc. Thus, the required length of the cable 1050 is a function of the maximum desired predetermined distance. In some implementations, the sanitizing system 1000 further includes a sensor (not shown) configured to determine a distance between the lower end 1046 of the lamp assembly 1040 and the closed bottom of the laundry sling to aid in determining an unwind time or number of rotations to sufficient unwind the cable 1050.

With the lamp assembly 1040 positioned within at least a portion of the laundry sling, the controller 1070 actuates the sanitizing lamp 1042 to cause the sanitizing lamp 1042 to emit a sanitizing wavelength of light (e.g., a UV-producing wavelength of light then an o-zone gas producing wavelength of light). Alternatively, the controller 1070 can actuate the sanitizing lamp 1042 responsive to, or during, movement of the lamp assembly 1040 from the retracted position (FIG. 10A) to the extended position (FIG. 10B). The controller 1070 also actuates the fan 1060 to move air adjacent to the sanitizing lamp 1042 to cause the air and the volume of produced o-zone gas to exit the housing 1010 and/or mix within the laundry sling to aid in substantially sanitizing the interior surface of the laundry sling.

After a predetermined sanitizing period (e.g., between about one second and about one minute, between about five seconds and ten seconds, between about five seconds and about twenty seconds, between about five seconds and fifty seconds, and/or between about five seconds and 110 seconds), the controller 1070 actuates the motor 1020 to rotate in a second direction that is opposite the direction used to unwind the cable 1050 (e.g., clockwise or counterclockwise) to wind the cable 1050 back onto or into the winding device 1030, causing corresponding linear movement of the lamp assembly 1040 in the opposite direction of arrow C. The motor 1020 continues to rotate in the second direction until the lamp assembly 1040 returns to the retracted position (FIG. 10A). The motor 1020 can be rotated in the second direction at the same speed or a different speed as when rotated in the first direction to unwind the cable 1050 (e.g., the cable 1050 is unwound at a first speed and the cable 1050 is wound at a second speed that is greater than the first speed).

Once the cable 1050 is wound such that the lamp assembly 1040 is removed from the laundry sling, the controller 1070 actuates the stopper to permit further movement of the laundry sling along the one or more support rails.

Like the sanitizing systems 1, 200, 800, the sanitizing system 1000 is suspended above one or more support rails to sanitize a laundry sling(s) that are moveable along the one or more support rails. For example, the upper end 1012 of the housing 1010 can be coupled to a ceiling of a structure and/or another support structure which is itself coupled to or suspended from a ceiling of a structure (e.g., an I-beam, another support rail, or the like). The housing 1010 is suspended such that the housing 1010 is generally perpendicular to the support rail and such that the lower end 1014 of the housing 1010 is positioned generally adjacent to the support rail. In some implementations, the sanitizing system 1000 is used with the laundry transport system 100 described herein (FIG. 1), which includes two support rails 110a and 110b. In other implementations, the sanitizing system 1000 can be used with the laundry transport system 800 (FIGS. 9A and 9B), which only includes support rail 810. In such implementations, the housing 1010 is suspended above the laundry transport system 800 such that a central axis of the lamp assembly 1040 is offset from the support rail 810 so that the lamp assembly 1040 will not contact the support rail 810 during operation.

Advantageously, when suspended above one or more support rails, the height of the housing 1010 of the sanitizing system 1000 is about half the height of the outer housing 710 of the sanitizing system 700. As a result, the sanitizing system 1000 can be installed with less overhead restrictions than the sanitizing system 700. In other words, the sanitizing system 1000 can be mounted in locations along a laundry transport system with less space between the one or more support rails and the ceiling. Relatedly, compared to the sanitizing system 700, the fan 1060 of the sanitizing system 1000 is closer to the lower opening 1016 of the lower end 1014 of the housing 1010, which further aids in dispersing and mixing the produced o-zone gas from the sanitizing lamp within the laundry sling. Further, because the sanitizing system 1000 uses the motor 1020 to extend and retract the sanitizing lamp 1042, unlike the sanitizing systems 1, 200, 700 described herein, the sanitizing system 1000 does not require a connection to a fluid reservoir (e.g., a compressed air supply), allowing the sanitizing system 1000 to be installed without regard to its location relative to a fluid reservoir and/or without connection tubes between the system 1000 and a fluid reservoir.

Although the sanitizing systems 1, 200, 700, 1000 of the present disclosure are shown and described as being used to sanitize a laundry sling, the same, or similar, systems can be used to substantially sterilize and disinfect other surfaces. For example, such systems can be used to sanitize other types of containers suspended from a rail support system that is similar to the first and second support rails 110a, 110b of the exemplary laundry transport system 100 (e.g., contaminated containers in a food processing facility, contaminated containers in a medical facility, or the like). Rather than sanitizing containers suspended from a rail support system, the same, or similar, systems can be used to sanitize containers moved beneath the sanitizing system by a conveyor belt or a similar mechanism. Further, sanitizing systems that are the same as or similar to the sanitizing systems 1, 200, 700, 1000 can be used to sanitize a volume of liquid stored in a container. For example, such sanitizing systems can be used to substantially sterilize water stored in containers in a water treatment plant.

While the disclosure is susceptible to various modifications and alternative forms, specific embodiments and methods thereof have been shown by way of example in the drawings and are described in detail herein. It should be understood, however, that it is not intended to limit the disclosure to the particular forms or methods disclosed, but, to the contrary, the intention is to cover all modifications, equivalents and alternatives falling within the spirit and scope of the disclosure.

What is claimed is:

1. A system for sanitizing a laundry sling that is moveable along one or more support rails, the system comprising:
    an outer housing having an upper portion and a lower portion;
    an inner track coupled to the outer housing;
    a transport mechanism coupled to the inner track such that the transport mechanism is moveable relative to the inner track between a first position and a second position;
    a sanitizing lamp coupled to the transport mechanism such that movement of the transport mechanism from the first position to the second position causes a corresponding movement of the sanitizing lamp;
    an actuator coupled to the inner track and the transport mechanism, the actuator being configured to cause the transport mechanism to move from the first position to the second position such that at least a portion of the sanitizing lamp protrudes from the lower portion of the outer housing and is positioned within the laundry sling; and
    a stopper coupled to one of the one or more support rails, the stopper being configured to inhibit movement of the laundry sling along the one or more support rails.

2. The system of claim 1, wherein the sanitizing lamp is configured to emit a sanitizing wavelength of light that substantially sterilizes an interior surface of the laundry sling.

3. The system of claim 2, wherein the sanitizing wavelength of light emitted from the sanitizing lamp is between about 180 nm and about 260 nm.

4. The system of claim 2, wherein the sanitizing wavelength emitted from the sanitizing lamp is between about 180 nm and about 190 nm and is configured to produce a volume of o-zone gas to aid in substantially sanitizing the interior surface of the laundry sling.

5. The system of claim 4, further comprising a fan coupled to the upper portion of the outer housing, the fan being configured to move air adjacent to the sanitizing lamp, thereby causing the air and the volume of o-zone gas produced by the sanitizing wavelength of light to mix within the laundry sling to aid in substantially sanitizing the interior surface of the laundry sling.

6. The system of claim 1, wherein the transport mechanism includes a support member, a first pair of opposing wheels coupled to the support member via a first support bracket, and a second pair of opposing wheels coupled to the support member via a second support bracket.

7. The system of claim 6, wherein each of the first pair of opposing wheels and the second pair of opposing wheels include a tongue protruding from an outer surface thereof, the tongue of each of the first pair of opposing wheels and the second pair of opposing wheels being configured to engage corresponding opposing grooves of the inner track to aid in coupling the transport mechanism to the inner track.

8. The system of claim 1, wherein the actuator includes a piston cylinder and a piston slidably disposed within the piston cylinder, the piston being coupled to the transport mechanism such that movement of the piston relative to the piston cylinder causes corresponding movement of the transport mechanism.

9. The system of claim 1, wherein (i) the laundry sling includes a body portion and a support ring, the body portion having an upper opening and a closed bottom, and (ii) the sanitizing lamp includes a proximal end and a distal end, the proximal end being coupled to the transport mechanism such that responsive to the transport mechanism being in the second position, the distal end of the sanitizing lamp is positioned within the body portion of the laundry sling at a predetermined distance from the closed bottom.

10. The system of claim 9, wherein the predetermined distance is at least 80% of a distance between the upper opening and the closed bottom of the body portion of the laundry sling.

11. The system of claim 9, wherein the predetermined distance is at least 50% of a distance between the upper opening and the closed bottom of the body portion of the laundry sling.

12. The system of claim 1, further comprising a sensor configured to determine the position of the laundry sling along the one or more support rails relative to the outer housing and cause the stopper to inhibit movement of the laundry sling responsive to determining that the laundry sling is positioned generally adjacent to the lower portion of the outer housing.

13. The system of claim 12, further comprising:
    a controller communicatively coupled to the stopper, the sensor, the actuator, and the sanitizing lamp, the controller being configured to automatically cause:
        (i) the stopper to inhibit movement of the laundry sling along the one or more support trails responsive to the sensor determining that the laundry sling is positioned generally adjacent to the lower portion of the outer housing;
        (ii) the actuator to cause the transport mechanism to move to the second position;
        (iii) the sanitizing lamp to provide a sanitizing illumination for a predetermined sanitizing period;
        (iv) the actuator to cause the transport mechanism to move to the first position; and
        (v) the stopper to permit movement of the laundry sling along the one or more support rails subsequent to the predetermined sanitizing period.

* * * * *